United States Patent
Hibner

(10) Patent No.: US 7,276,032 B2
(45) Date of Patent: Oct. 2, 2007

(54) BIOPSY APPARATUS AND METHOD

(75) Inventor: John A. Hibner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 69 days.

(21) Appl. No.: 10/953,904

(22) Filed: Sep. 29, 2004

(65) Prior Publication Data

US 2006/0074346 A1    Apr. 6, 2006

(51) Int. Cl.
*A61B 10/00* (2006.01)
(52) U.S. Cl. .................................. 600/564
(58) Field of Classification Search ........ 600/562–568; 606/167, 170
See application file for complete search history.

(56) References Cited

U.S. PATENT DOCUMENTS

| | | | |
|---|---|---|---|
| 3,994,297 A | 11/1976 | Kopf | |
| 5,526,822 A * | 6/1996 | Burbank et al. | 600/567 |
| 5,649,547 A | 7/1997 | Ritchart et al. | |
| 5,720,717 A | 2/1998 | D'Andree | |
| 5,827,305 A | 10/1998 | Gordon | |
| 5,971,911 A | 10/1999 | Wilk | |
| 6,042,593 A | 3/2000 | Storz et al. | |
| 6,428,486 B2 * | 8/2002 | Ritchart et al. | 600/566 |
| 6,485,436 B1 * | 11/2002 | Truckai et al. | 600/564 |
| 6,488,659 B1 | 12/2002 | Rosenman | |
| 6,540,713 B1 | 4/2003 | Cimino | |
| 6,572,529 B2 | 6/2003 | Wilk | |
| 6,726,654 B2 | 4/2004 | Rosenman | |
| 2001/0041821 A1 | 11/2001 | Wilk | |
| 2003/0199787 A1 | 10/2003 | Schwindt | |
| 2004/0153003 A1 * | 8/2004 | Cicenas et al. | 600/564 |
| 2004/0158227 A1 | 8/2004 | Nash et al. | |
| 2004/0167428 A1 * | 8/2004 | Quick et al. | 600/564 |
| 2004/0199115 A1 | 10/2004 | Rosenman | |
| 2005/0065453 A1 * | 3/2005 | Shabaz et al. | 600/564 |
| 2005/0075581 A1 | 4/2005 | Schwindt | |
| 2005/0203439 A1 * | 9/2005 | Heske et al. | 600/566 |
| 2006/0074346 A1 | 4/2006 | Hibner | |

FOREIGN PATENT DOCUMENTS

EP    1433423    6/2004

OTHER PUBLICATIONS

European Search Report dated May 18, 2006 for corresponding patent application, European Patent Application No. 05256053.9 (END5471USNP).

* cited by examiner

*Primary Examiner*—Max F. Hindenburg
*Assistant Examiner*—Brian Szmal

(57) ABSTRACT

A biopsy device and method are provided for obtaining a tissue sample, such as breast tissue biopsy sample. The device includes an outer cannula having a cutter lumen and a side tissue port communicating with the cutter lumen. The device can be operated to push severed tissue samples through the cutter with a fluid, such as saline, without exposing the tissue surrounding the cannula to the fluid.

8 Claims, 28 Drawing Sheets

BIOPSY APPARATUS AND METHOD

CROSS REFERENCE TO RELATED APPLICATIONS

This applications cross references and incorporates by reference the following commonly assigned patent applications: U.S. application Ser. No. 10/785,755 "Biopsy Device with Variable Speed Cutter Advance" filed Feb. 24, 2004 in the name of Thompson et al.; U.S. patent application Ser. No. 10/676,944 "Biopsy Instrument with Internal Specimen Collection Mechanism" filed Sep. 30, 2003 in the name of Hibner et al.; and U.S. patent application Ser. No. 10/732,843 "Biopsy Device with Sample Tube" filed Dec. 10, 2003 in the name of Cicenas et al.

FIELD OF THE INVENTION

The present invention relates in general to biopsy devices, and more particularly to biopsy devices having a cutter for severing tissue.

BACKGROUND OF THE INVENTION

The diagnosis and treatment of tissue is an ongoing area of investigation. Medical devices for obtaining tissue samples for subsequent sampling and/or testing are know in the art. For instance, a biopsy instrument now marketed under the tradename MAMMOTOME is commercially available from Ethicon Endo-Surgery, Inc. for use in obtaining breast biopsy samples.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996, and U.S. Patent Application 2003/0199753 published Oct. 23, 2003 to Hibner et al.

Researchers in the medical device area continue to seek new and improved methods and devices for cutting, handling, and storing tissue samples.

SUMMARY OF THE INVENTION

In one embodiment, the present invention provides a biopsy method. A biopsy device having an outer outer cannula having a cutter lumen and a side tissue port communicating with the cutter lumen can be provided. A hollow cutter can be disposed within the cutter lumen. Tissue can be drawn into the side tissue port, such as by vacuum. The cutter can be translated past the side tissue port to sever a tissue sample. The severed tissue sample can then be pushed through the cutter with a fluid such that the tissue surrounding the outer cannula is not exposed to the fluid. In one embodiment, the cutter can act to close off the side tissue port to prevent the tissue surrounding the outer cannula from being exposed to the fluid used to push the sample through the cutter.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

The present invention pertains to a biopsy device for obtaining a tissue sample from within a body. The biopsy device can have a reduced cutting stroke length as compared to device such as commercially available Mammotome brand biopsy devices. Reducing the cutting stroke length decreases the time to acquire each sample, and also the overall size of the biopsy device, thereby enhancing the versatility and ergonomics of the device. The reduced stroke length of the cutter enables many of the same probe components to be used in all three primary imaging environments: mammography, ultrasound and MRI. In addition, the present invention enables the sequential collection and storage of tissue samples. Tissue samples may be removed from the biopsy device and examined in real-time, as well as sequentially stored for subsequent retrieval at the conclusion of the biopsy procedure. Sequentially storing tissue samples eliminates the need to immediately remove each sample from the device following sampling, thereby further reducing the sample acquisition time.

Figure 1:
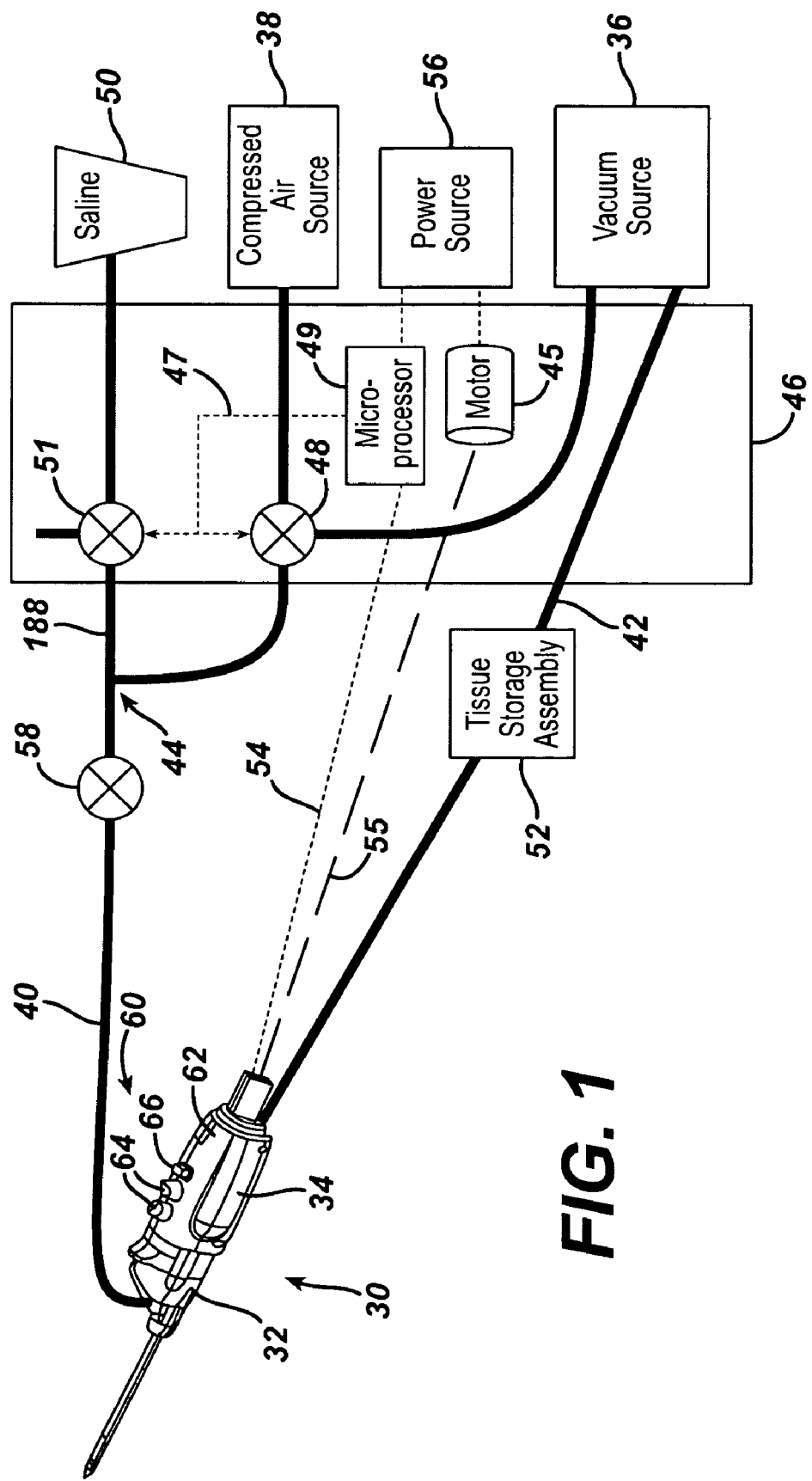
FIG. 1 is a partial isometric and partial schematic view of a biopsy instrument according to one embodiment of the present invention, which includes a handpiece for the collection of soft tissue.

FIG. 1 shows a core sampling biopsy instrument according to the present invention comprising a handpiece identified generally as numeral 30. Handpiece 30 can be held comfortably in a single hand, and can be manipulated with a single hand. Handpiece 30 can include a probe assembly 32 and a detachably connected holster 34. Probe assembly 32 can be operatively connected to a vacuum source 36, such as by a first, lateral tube 40 and a second, axial tube 42. First and second tubes 40, 42 can be made from a flexible, transparent or translucent material, such as silicon tubing, PVC tubing or polyethylene tubing. Using a transparent material enables visualization of the matter flowing through tubes 40, 42.

First tube 40 can inclubee a Y connector 44 for connecting to multiple fluid sources. A first proximal end of Y connector 44 can extend to a first solenoid controlled rotary valve 48 in a control module 46, while the second proximal end of the Y connector can extend to a second solenoid controlled rotary valve 51 in control module 46. The first solenoid controlled rotary valve 48 in control module 46 can be operable to connect either the vacuum source 36 or the compressed air source 38 to lateral tube 40. It is understood within this specification that compressed air means air pressure at or above atmospheric pressure. In one configuration, when valve 48 is activated, vacuum is supplied to tube 40 from vacuum source 36, and when valve 48 is not activated, pressurized air from compressed air source 38 is supplied through tube 40. The solenoid associated with valve 48 can be controlled by a microprocessor 49 in control module 46, as indicated by dashed line 47. Microprocessor 49 can be employed to adjust the position of valve 48 automatically based upon the position of a cutter movably supported within probe assembly 32. The second solenoid controlled rotary valve 51 in control module 46 can be employed to either connect a saline supply 50 (such as a saline supply bag, or alternatively, a pressurized reservoir of saline) to a tube 188 or to seal off the proximal end of tube 188. For instance, rotary valve 51 can be activated by microprocessor 49 to supply saline when a switch on handpiece 30 is actuated. When rotary valve 51 is activated, first rotary valve 48 can be automatically deactivated (such as by microprocessor 49) to prevent the interaction of vacuum and saline within lateral tube 40. A stopcock 58 may be included in lateral vacuum tube 40 to allow for a syringe injection of saline directly into the tube 40, if desired. For instance, a syringe injection can be employed to increase the saline pressure in the tube to dislodge any clogs that may occur, such as tissue clogging fluid passageways.

In one embodiment, axial vacuum tube 42 can be employed to communicate vacuum from source 36 to probe assembly 32 through a tissue storage assembly 52. Axial tube 42 can provide vacuum through the cutter within probe assembly 32 to assist in prolapsing tissue into a side tissue aperture aperture prior to cutting. After cutting occurs, the vacuum in axial line 42 can be employed to help draw a severed tissue sample from probe assembly 32 and into tissue storage assembly 52, as will be described in further detail below.

Holster 34 can include a control cord 54 for operationally connecting handpiece 30 to control module 46, and a flexible rotatable shaft 55 connecting the holster to a drive motor 45. A power source 56 can be employed to provide energy to control module 46 for powering holster 34 via control cord 54. Switches 60 are mounted on holster upper shell 62 to enable an operator to use handpiece 30 with a single hand. One-handed operation allows the operator's other hand to be free, for example, to hold an ultrasonic imaging device. Switches 60 can include a two-position rocker switch 64 for manually actuating the motion of the cutter (e.g. forward movement of the rocker switch moves the cutter in the forward (distal) direction for tissue sampling and rearward movement of the rocker switch actuates the cutter in the reverse (proximal) direction). Alternatively, the cutter could be automatically actuated by control module 46. An additional switch 66 can be provided on holster 34 for permitting the operator to activate saline flow on demand into lateral tube 40 (for instance, switch 66 can be configured to operate valve 51 for providing saline flow to tube 40 when switch 66 is depressed by the user).

Figure 2:
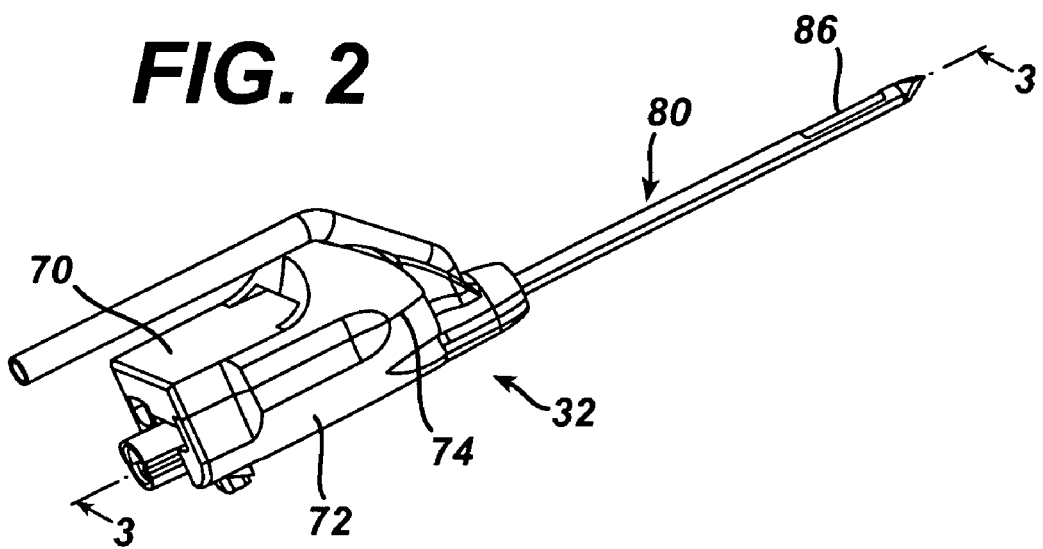
FIG. 2 is an isometric view of the probe assembly separated from the holster.

FIG. 2 shows probe assembly 32 disconnected from holster 34. Probe assembly 32 includes an upper shell 70 and a lower shell 72, each of which may be injection molded from a rigid, biocompatible plastic, such as a polycarbonate. Upon final assembly of probe assembly 32, upper and lower shells 70, 72 can be joined together along a joining edge 74 by any of a number of methods well-known for joining plastic parts, including, without limitation, ultrasonic welding, snap fasteners, interference fit, and adhesive joining.

Figure 3A:
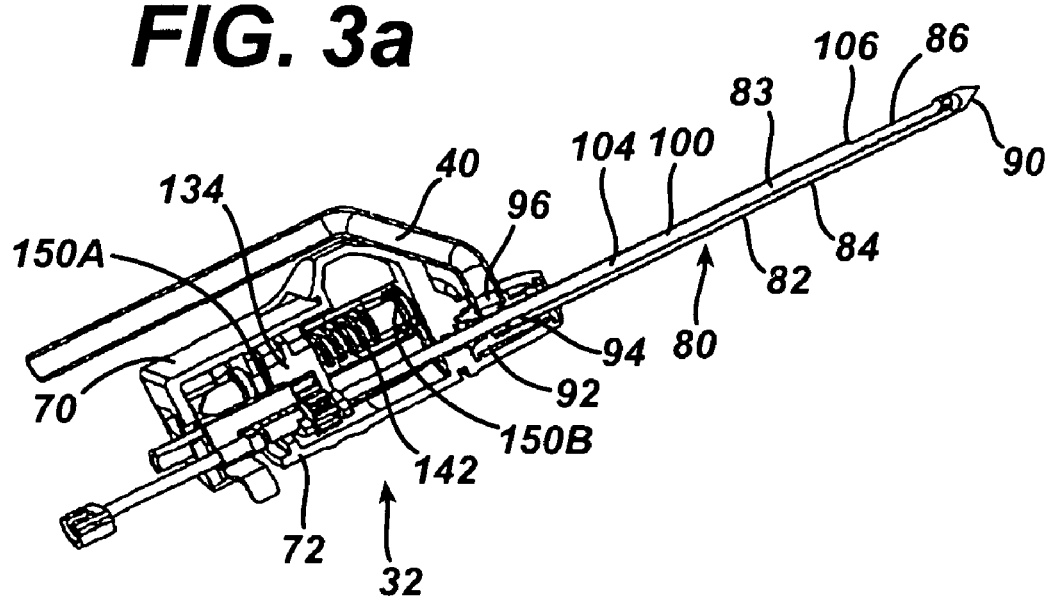
FIG. 3a is cross-sectional isometric view of the probe assembly taken along line 3—3 in FIG. 2 with the cutter & carriage assembly positioned at the proximal end position.
Figure 3B:
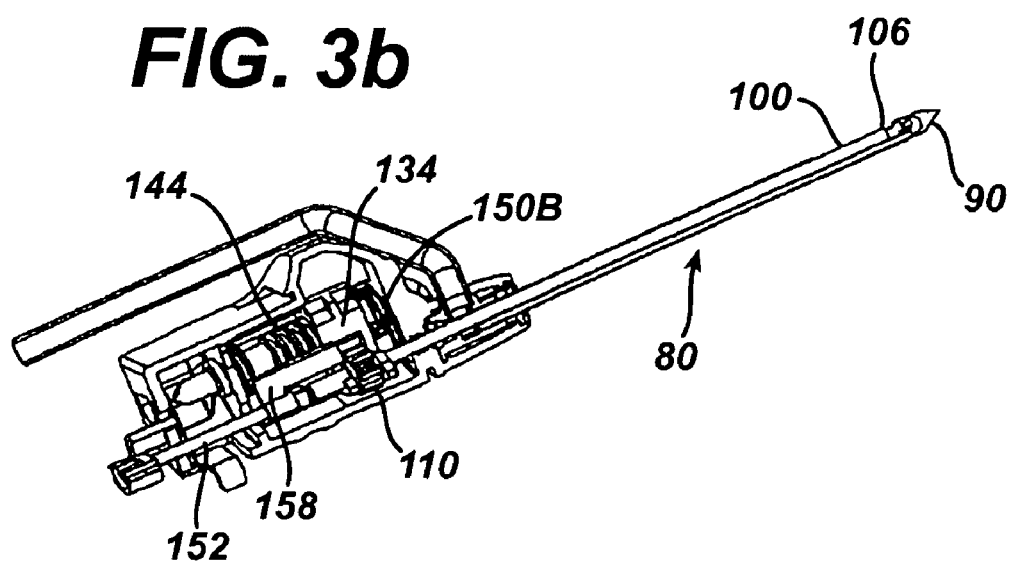
FIG. 3b is cross-sectional isometric view of the probe assembly taken along line 3—3 in FIG. 2 with the cutter & carriage assembly positioned between the proximal and distal end positions.
Figure 3C:
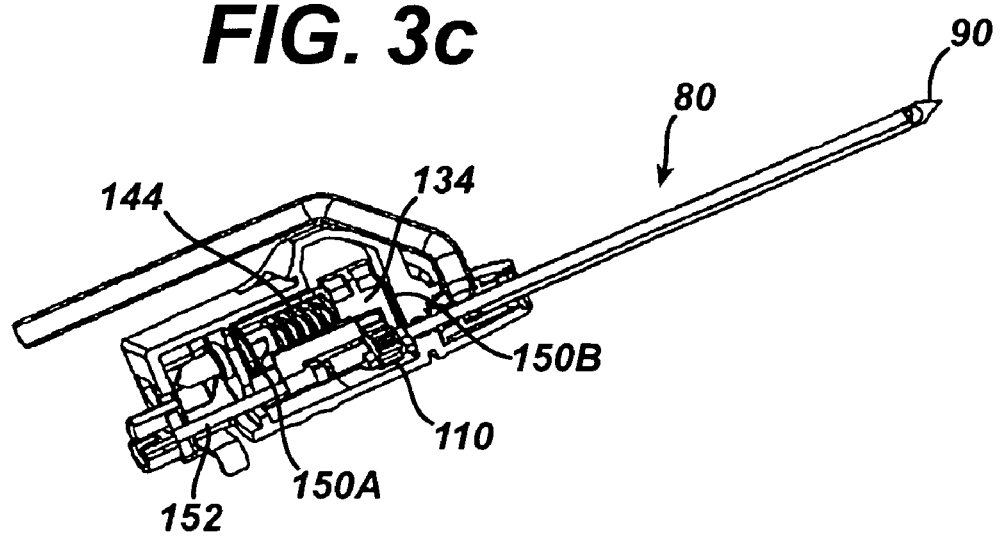
FIG. 3c is cross-sectional isometric view of the probe assembly taken along line 3—3 in FIG. 2 with the cutter & carriage assembly positioned at the distal end position.
Figure 4:
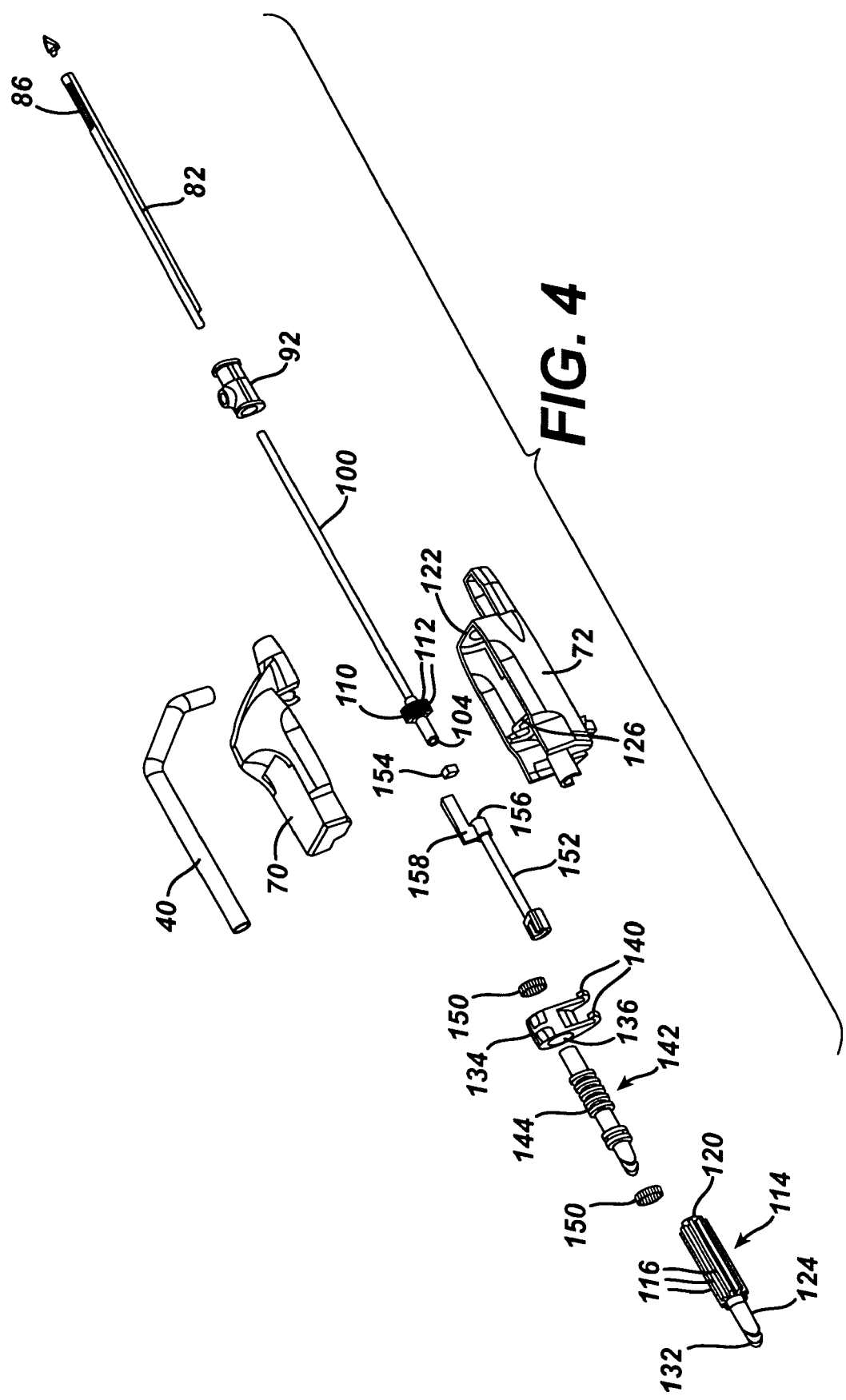
FIG. 4 is an exploded isometric view of the probe assembly of FIG. 2.
Figure 5A:
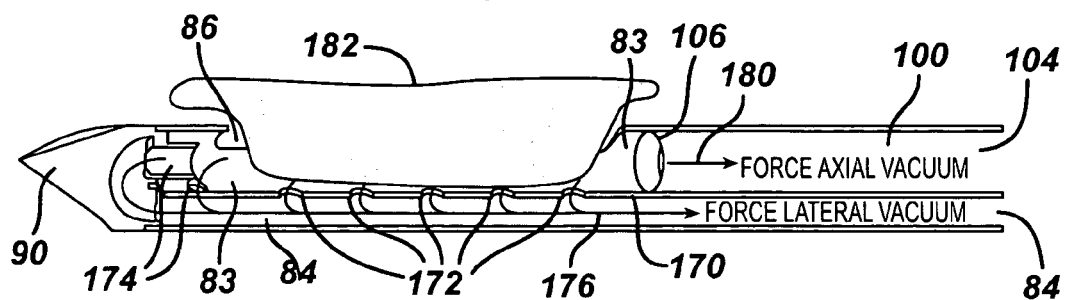
FIG. 5a is a schematic diagram of the biopsy needle illustrating the fluid forces and cutter when the cutter is in a proximal end position at the initiation of a cutting cycle.

FIGS. 3a, 3b, 3c, and 4 illustrate probe assembly 32 in greater detail. FIG. 3a depicts the cutter assembly and carriage retracted proximally. FIG. 3b depicts the cutter assembly and carriage partially advanced. FIG. 3c depicts the cutter assembly and carriage advanced distally. As shown in FIGS. 3a–c, the probe assembly can include a biopsy needle 80 located at a distal end of probe assembly 32 for insertion into a patient's skin to obtain a tissue sample. Needle 80 comprises an elongated, metallic cannula 82, which can include an upper lumen, such as an upper cutter lumen 83 for receiving a cutter 100 (as shown in FIG. 5a), and a lower lumen, such as a lower lumen 84 for providing a fluid passageway. Cutter 100 can be disposed within cannula 82, and can be coaxially disposed within lumen 83.

Cannula 82 can have any suitable cross-sectional shape, including a circular or oval shaped cross-section. Adjacent and proximal of the distal end of cannula 82 is a side (lateral) tissue receiving port 86 for receiving the tissue to be severed from the patient. A sharpened tip of needle 80 can be formed by a separate endpiece 90 attached to the distal end of cannula 82. The sharpened tip of endpiece 90 can be used to pierce the patients skin so that the side tissue receiving port can be positioned in the tissue mass to be sampled. Endpiece 90 can have a two-sided, flat-shaped point as shown, or any number of other shapes suitable for penetrating the soft tissue of the patient.

The proximal end of needle 80 can be attached to a union sleeve 92 having a longitudinal bore 94 therethrough, and a transverse opening 96 into a widened center portion of the bore. The distal end of lateral tube 40 can be inserted to fit tightly into transverse opening 96 of union sleeve 92. This attachment allows the communication of fluids (gas or liquid) between the lower lumen and the lateral tube 40.

The cutter 100, which can be an elongated, tubular cutter, can be disposed at least partially within upper lumen 83, and can be supported for translation and rotation within lumen 83. Cutter 100 can be supported within needle lumen 84 so as to be translatable in both the distal and proximal directions. Cutter 100 can have a sharpened distal end 106 for cutting tissue received in upper lumen 83 through side tissue receiving port 86. The cutter 100 may be formed of any suitable material, including without limitation a metal, a polymer, a ceramic, or a combination of materials. Cutter 100 can be translated within lumen 83 by a suitable drive assembly such that distal end 106 travels from a position proximal of the side tissue port 86 (illustrated in FIG. 3a) to a position distal of side tissue port 86 (illustrated in FIG. 3c), in order to cut tissue received in lumen 83 through the side tissue port 86. In an alternative embodiment, an exterior cutter can be employed, with the exterior cutter sliding coaxially with an inner cannular needle, and the inner needle can include a side tissue receiving port.

Figure 5B:
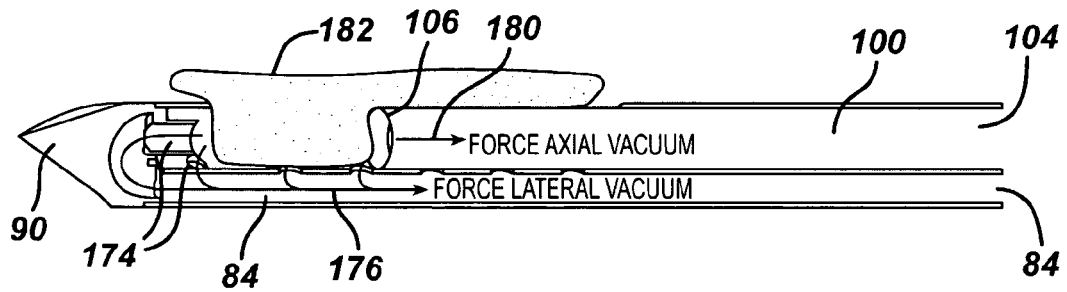
FIG. 5b is a schematic diagram similar to FIG. 5a, illustrating the cutter and fluid forces as the cutter translates distally to sever a tissue sample.
Figure 5C:
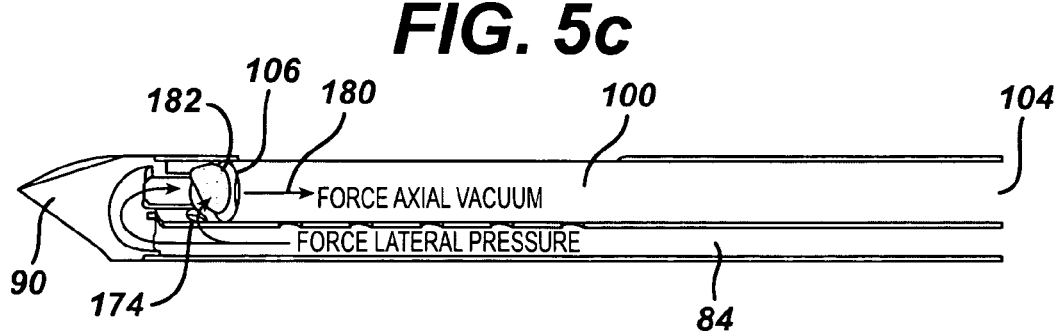
FIG. 5c is a schematic diagram similar to FIG. 5a, illustrating the fluid forces and cutter when the cutter has closed the aperture and severed the tissue sample.

Union sleeve 92 is supported between probe upper and lower shells 70, 72 to ensure proper alignment between cutter 100 and the union sleeve. The cutter 100 can be a hollow tube, with a lumen 104 extending axially through the length of cutter 100. As shown in FIG. 4, the proximal end of cutter 100 can extend through an axial bore of a cutter gear 110. Cutter gear 110 may be metallic or polymeric, and includes a plurality of cutter gear teeth 112. Cutter gear 110 can be driven by a rotary drive shaft 114 having a plurality of drive gear teeth 116 designed to mesh with cutter gear teeth 112. Drive gear teeth 116 can extend along the length of drive shaft 114 so as to engage cutter gear teeth 112 as the cutter 100 translates from a proximal most position to a distal most position, as illustrated in FIGS. 5a–5c. Drive gear teeth 116 can be in continual engagement with cutter gear teeth 112 to rotate cutter 100 whenever drive shaft 114 is rotatably driven. Drive shaft 114 rotates cutter 100 as the cutter advances distally through tissue receiving port 86 for the cutting of tissue. Drive shaft 114 may be injection molded from a rigid engineered plastic such as liquid crystal polymer material or, alternatively, could be manufactured from a metallic or non-metallic material. Drive shaft 114 includes a first axial end 120 extending distally from the shaft. Axial end 120 is supported for rotation within probe lower shell 72, such as by a bearing surface feature 122 molded on the inside of the probe shell. Similarly, a second axial end 124 extends proximally from rotary drive shaft 114 and is supported in a second bearing surface feature 126 which can also be molded on the inside of probe lower shell 72. An O-ring and bushing (not shown) may be provided on each axial end 120, 124 to provide rotational support and audible noise dampening of the shaft 114 when rotary drive shaft 114 is mounted in probe shell 72.

As shown in FIGS. 3a, 3b, 3c, and 4, a drive carriage 134 is provided in probe assembly 32 to hold cutter gear 110, and carry the cutter gear and attached cutter 100 during translation in both the distal and proximal directions. Drive carriage 134 is preferably molded from a rigid polymer and has a cylindrically-shaped bore 136 extending axially therethrough. A pair of J-shaped hook extensions 140 extend from one side of drive carriage 134. Hook extensions 140 rotatably support cutter 100 on either side of cutter gear 110 to provide proximal and distal translation of the cutter gear and cutter during proximal and distal translation of drive carriage 134. Hook extensions 140 align cutter 100 and cutter gear 110 in the proper orientation for cutter gear teeth 112 to mesh with drive gear teeth 116.

Drive carriage 134 is supported on a translation shaft 142. Shaft 142 is supported generally parallel to cutter 100 and rotary drive shaft 114. Rotation of the translation shaft 142 provides translation of the carriage 134 (and so also cutter gear 110 and cutter 100) by employing a lead screw type drive. Shaft 142 includes an external lead screw thread feature, such as lead screw thread 144, on its outer surface. The screw thread 144 extends into a bore 136 in carriage 134. The screw thread 144 engages an internal helical threaded surface feature provided on the inner surface of bore 136. Accordingly, as shaft 142 is rotated, the carriage 134 translates along the threaded feature 144 of the shaft 142. The cutter gear 110 and the cutter 100 translate with the carriage 134. Reversing the direction of rotation of shaft 142 reverses the direction of translation of the carriage 134 and the cutter 100. Translation shaft 142 may be injection molded from a rigid engineered plastic such as liquid crystal polymer material or, alternatively, could be manufactured from a metallic or non-metallic material. Translation shaft 142 with lead screw thread feature 144 can be molded, machined, or otherwise formed. Likewise, carriage 134 can be molded or machined to include an internal helical thread in bore 136. Rotation of shaft 142 drives the carriage and cutter gear 110 and cutter 100 in the distal and proximal directions, depending upon the direction of rotation of shaft 142, so that cutter 100 translates within probe assembly 32. Cutter gear 110 is rigidly attached to cutter 100 so that the cutter translates in the same direction and at the same speed as drive carriage 134.

In one embodiment, at the distal and proximal ends of lead screw thread 144, the helical thread is cut short so that the effective pitch width of the thread is zero. At these distal most and proximal most positions of thread 144, translation of drive carriage 134 is no longer positively driven by shaft 142 regardless of the continued rotation of shaft 142, as the carriage effectively runs off the thread 144. Biasing members, such as compression coil springs 150A and 150B (FIGS. 3a–c), are positioned on shaft 142 adjacent the distal and proximal ends of the screw thread 144. Springs 150A/B bias carriage 134 back into engagement with lead screw thread 144 when the carriage runs off the thread 144. While shaft 142 continues rotating in the same direction, the zero pitch width thread in combination with springs 150A/B cause carriage 134 and, therefore, cutter 100 to "freewheel" at the end of the shaft. At the proximal end of the threaded portion of shaft 142, the carriage engages spring 150A. At the distal end of the threaded portion of shaft 142, the carriage engages spring 150B. When the carriage runs off the screw thread 144, the spring 150A or 150B engages the carriage 134 and biases the carriage 134 back into engagement with the screw thread 144 of shaft 142, at which point continued rotation of the shaft 142 again causes the carriage 134 to run off the screw thread 144. Accordingly, as long as rotation of shaft 142 is maintained in the same direction, the carriage 134 (and cutter 100) will continue to "freewheel", with the distal end of the cutter 106 translating a short distance proximally and distally as the carriage is alternately biased onto the thread 144 by spring 150A or 150B and then run off the screw thread 144 by rotation of shaft 142. When the cutter is in the distal most position shown in FIG. 3c, with the distal end 106 of cutter positioned distal of side tissue port 86, spring 150B will engage carriage 134, and repeatedly urge carriage 134 back into engagement with screw thread 144 when carriage 134 runs off the screw thread 144. Accordingly, after the cutter 100 is advanced such that the distal end 106 of the cutter translates distally past the side tissue port 86 to cut tissue, to the position shown in FIG. 3c, continued rotation of the shaft 142 will result in the distal end 106 oscillating back and forth, translating a short distance proximally and distally, until the direction of rotation of shaft 142 is reversed (such as to retract the cutter 100 distally to the position shown in FIG. 3a.) The slight movement of carriage 134 into engagement with the screw thread and out of engagement with the screw thread 144 against the biasing force of spring 150B, causes the distal end 106 of cutter 100 to repetitively reciprocate a short distance within cannula 82, which distance can be about equal to the pitch of threads 144, and which distance is shorter than the distance the cutter travels in crossing the side tissue port 86. This reciprocal movement of the cutter can provide alternate covering and uncovering of at least one fluid passageway disposed distally of the side tissue port, as described below.

The zero pitch width ends of lead screw thread 144 provide a defined stop for the axial translation of cutter 100, thereby eliminating the need to slow carriage 134 (i.e. cutter 100) as it approaches the distal and proximal ends of the thread. This defined stop reduces the required positioning accuracy for carriage 134 relative to shaft 142, resulting in reduced calibration time at the initialization of a procedure. The freewheeling of carriage 134 at the distal and proximal most positions of translation shaft 142 eliminates the need to rotate the shaft a precise number of turns during a procedure. Rather, translation shaft 142 only needs to translate at least a minimum number of turns to insure carriage 134 has translated the entire length of lead screw thread 144 and into the zero width thread. Additionally, the freewheeling of carriage 134 eliminates the need to home the device, allowing probe assembly 32 to be inserted into the patient's tissue without first being attached to holster 34. After probe assembly 32 is inserted, holster 34 is attached and sampling can be commenced.

As shown in FIG. 4, a non-rotating rear tube 152 can be provided which tube 152 can extend proximally from the proximal end of cutter 100 just proximal of cutter gear 110. Rear tube 152 can be hollow and can have substantially the same inner diameter as cutter 100, and may be comprised of the same material as the cutter. A seal 154 can be positioned between cutter 100 and rear tube 152 to enable the cutter to rotate relative to the tube while providing a pneumatic seal between the rear tube 152 and the cutter 100. A rear lumen 156 can extend through the length of tube 152 and can be aligned with lumen 104 in cutter 100. Rear lumen 156 transports excised tissue samples from lumen 104 through probe assembly 32 to the tissue storage assembly 52. Lumen 104 and rear lumen 156 are axially aligned to provide a continuous, generally straight line, unobstructed passageway between tissue receiving port 86 and tissue storage assembly 52 for the transport of tissue samples. The inner surfaces of cutter 100 and tube 152 may be coated with a hydrolubricous material to aid in the proximal transport of the excised tissue samples.

A lateral extension 158 can be provided and can be supported by and extend distally from rear tube 152 for securing the tube to drive carriage 134. The extension 158 connects tube 152 to carriage 134 so that tube 152 translates with cutter 100, and maintains lumens 104, 156 in continuous fluid-tight communication throughout the cutting cycle.

FIGS. 5a–5d provide simplified schematic views of the movement of cutter 100 during a cutting cycle. As shown in FIG. 5a, initially in the cutting cycle cutter 100 is located at a proximal most position with distal cutting end 106 disposed proximally of the proximal most edge of the side tissue port 86, and adjacent the proximal end of a lumen divider 170. As the cutting cycle begins, a lateral vacuum force (indicated by arrow 176) can be provided in lower lumen 84. Vacuum force 176 can be transmitted from vacuum source 36 through tube 40 to lower lumen 84 through a flow path provided by union sleeve 92.

Figure 5D:
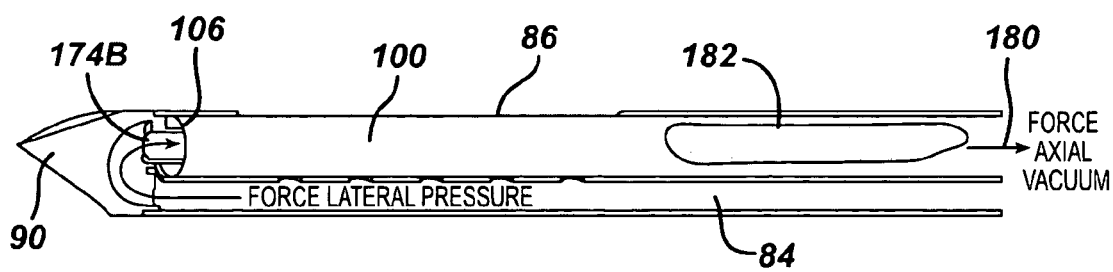
FIG. 5d is a schematic diagram similar to FIG. 5a, illustrating the fluid forces and cutter as the cutter has reached the distal end position and a tissue sample is aspirated to the tissue storing assembly at the conclusion of a cutting cycle.

Microprocessor 49 can be employed to activate valve 48 to supply vacuum force 176 when switch 64 is actuated by the user to begin moving cutter 100 distally within needle 80. Lateral vacuum force 176 communicates with tissue receiving port 86 through fluid passageways 172 disposed under port 86, and through one or more fluid passageways 174 disposed distally of the port 86. In FIG. 5c, a fluid passageway 174A is illustrated disposed distally of port 86 and spaced approximately 180 degrees circumferentially from port 86. In FIG. 5d, a fluid passageway 174B is illustrated disposed distally of the port 86 in the distal endpiece 90 of the biopsy probe. Both fluid passageways 174A and 174B can provide fluid communication between lower lumen 84 and upper lumen 83.

Lateral vacuum force 176 can be employed in combination with an axial vacuum force 180 through cutter lumen 104 to draw a tissue sample 182 into tissue port 86. After tissue sample 182 is drawn into port 86, cutter 100 can be rotated and simultaneously translated distally to sever the tissue sample from the surrounding tissue. While cutter 100 advances, vacuum forces 176, 180 can be maintained through lower lumen 84 and cutter lumen 104 to draw the tissue sample into the cutter lumen as the sample is severed. As shown in FIG. 5b, as cutter 100 advances the cutter slides across fluid passageways 172, successively blocking the lateral vacuum through the holes.

When cutter 100 reaches the distal most position, as shown in FIG. 5c, fluid passageways 172 can be completely blocked by the cutter. At this point in the cutting cycle, cutter rotation can be maintained, and the cutter can "freewheel" as described above, with the distal end 106 of the cutter 100 moving proximally and distally in an alternating, oscillating manner. As cutter 100 freewheels, the cutter can oscillate distally and proximally a distance which can be about equal to the pitch of lead screw thread 144 at a frequency corresponding approximately to the rotation speed of translation shaft 142. One or more fluid passageways 174A can be positioned in lumen divider 170 such that as cutter 100 is freewheeling at its distal most position, the cutter alternately covers and uncovers (and so opens and closes) the passageways 174A. With passageway 174A open, lower lumen 84 remains in fluid communication with cutter lumen 104 through divider 170 despite the blocking of passageways 172. The repetitive movement of cutter 100 over passageway 174A can assist in clearing any tissue that may be blocking or clogging passageway 174A, and to maintain fluid communication through passageway 174A.

Fluid Passageway 174B in distal endpiece 90 can be employed in place of or in combination with fluid passageway 174A. Fluid passageway 174B can provide fluid communication between lower lumen 84 and upper lumen 83 when passageway 174 is covered by cutter 100.

A predefined amount of time after the cutter 100 reaches its distal most position and begins to freewheel, the solenoid on rotary valve 48 can be deenergized or otherwise controlled by microprocessor 49 to replace lateral vacuum force 176 with forward pressurized air (either atmospheric or greater) as shown by the arrows in FIG. 5c. The pressurized air is discharged through lateral tube 40 to lumen 84. With port holes 172 closed off by cutter 100, the pressurized air communicates with upper lumen 83 through fluid passageway 174A (and/or a 174B) to apply a force against the distal face of sample 182. The force acting on the distal face of sample 182 can act in combination with an with axial vacuum force 180 provided through the lumen 104 of cutter 100. The push provided by the force acting on the distal face of the sample 182 in combination with the vacuum "pull" provided by the vacuum provided via the lumen 104 of cutter 100 can be employed to move the sample 182 into and through lumen 104 of cutter 100, as shown in FIG. 5d. Alternatively, instead of employing pressurized air to provide a force on the distal face of sample 182, a pressurized liquid, such as saline, can be directed through lower lumen 84 and fluid passageways 174A and/or 174B to provide the force on the distal face of sample 182. The cutter 100 closes the side tissue port 86 from the flow of fluid (gas or liquid) so that tissue surrounding the outer cannula and side port 86 is not exposed to the fluid.

As the tissue sample 182 translates proximally through probe assembly 32 towards sample collection assembly 52, the cutter 100 can be maintained in a distal most position. Alternatively, the cutter 100 can be retracted back through tissue port 86 towards its initial position in preparation for the next cutting cycle. After cutter 100 is fully retracted, and the tissue sample is translated to tissue storage assembly 52, lateral vacuum force 176 is again provided via lumen 84 to draw the next tissue sample into port 86. During the translation of cutter 100, the cutter can operate in conjunction with divider 170 to separate lumen 83 from lumen 84.

During the cutting cycle, cutter 100 translates from a point just proximal of side tissue receiving port 86 to a point just distal of the receiving port. The severed tissue samples are directed through the length of the lumen 104 of cutter 100 and out of the proximal end of the cutter 100, rather than translating the cutter (with the samples carried in the distal end of the cutter) proximally through the needle 80 to eject the samples with a knock-out pin, as in some prior devices. Accordingly, the cutting stroke length can be reduced to be just slightly longer than the length of the side tissue port 86. With the reduced stroke length, the distal end of the cutter 100 (as well as a length of the cutter 100) can remain within needle 80 throughout the cutting cycle, eliminating the need to accommodate the full length of the cutter within the probe housing and proximal of the needle 80. In addition, the reduced cutting stroke length reduces the required length of translation shaft 142, since the shaft need only translate the cutter a distance slightly longer than the length of tissue receiving port 86. Reducing the translation shaft length, and eliminating the need to accommodate the cutter length within the probe housing, enables the length of handpiece 30 to be reduced. The time to acquire each tissue sample is also reduced in the present invention, due to the shortened cutting stroke reducing the time required to advance and retract the cutter through needle 80. Since cutter 100 retracts only to a point just proximal of tissue receiving port 86, lumen divider 170 can be formed to extend to the proximal most point of the cutter, rather than through the entire length of the needle. Reducing the length of divider 170 reduces the required materials and cost of manufacturing needle 80.

As described above, fluid passageways 174A and/or 174B can also be used to apply saline to the distal face of a severed tissue sample, such as illustrated in FIGS. 5C–D. The saline may be used to provide a push against the tissue sample and thereby aid in moving the tissue sample proximally within the cutter lumen 104. To provide a saline flush, tubing from saline supply bag 50 is routed through rotary valve 51 by control module 46 to Y connector 44 and through lateral tube 40 to lumen 84. In one embodiment, a button can be provided on handpiece 30, such that when the button is depressed while the cutter is freewheeling in its distal most position, the valve 51 is activated to connect the saline 50 to lateral tube 40. Prior to a sampling procedure, the saline system may be primed by activating the rotary valve 51 to allow the vacuum from vacuum source 36 to draw saline into tubing 188. Saline will then fill tubing 188 up to Y connector 44. When the operator then depresses the handpiece button during the procedure, the saline will flow from Y connector 44, through lateral tube 40, and into lumen 84 to be applied against tissue sample 182. When rotary valve 51 is deenergized, tubing 188 is sealed off so that the flow of saline to lumen 84 is stopped.

In an alternative embodiment, saline can be automatically provided to lumen 84 during every cutting cycle. In this embodiment, a handpiece button is not required to operate the saline. Rather, microprocessor 49 automatically activates rotary valve 51 a designated time after cutter 100 reaches the distal most position within needle 80 during the cutting cycle, and deactivates the valve when the cutter has retracted to a designated proximal position. A position sensor can be incorporated with the holster 34 or control module 46 to activate rotary valve 51 based upon the axial position of the cutter in the cutting cycle. Thus, the position of the cutter 100 will automatically activate and deactivate rotary valve 51, such as when the cutter advances and retracts during each cutting cycle.

Figure 6:
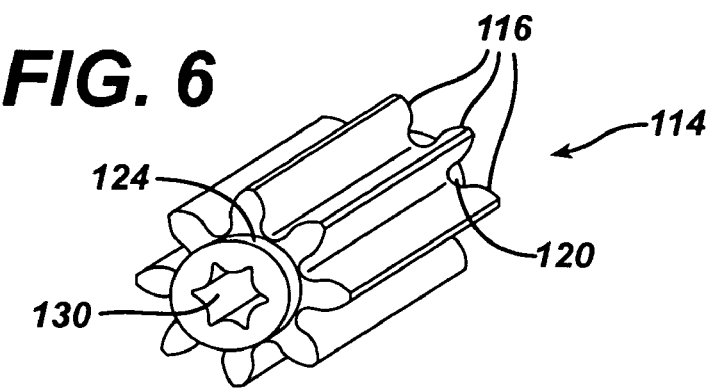
FIG. 6 is an isometric view of the rotary drive shaft illustrating a drive coupling configuration.

As shown in FIG. 4, a drive slot 132 may be formed in proximal end 124 of shaft 114 for interfacing with a similar-shaped drive slot in a motor drive shaft, or other rotary drive input from holster 34. Alternatively, as shown in FIG. 6, a star-shaped interface 130 may be molded into second axial end 124 of drive shaft 114. Star interface 130 can be provided to mate with a similar-shaped male interface which could be provided on the rotary drive shaft of holster 34 to rotate drive shaft 114. Alternatively, the female star interface 130 may be molded into the drive shaft from holster 34 and a similar-shaped male interface formed in drive shaft 114. Use of star interface 130, or another similar type of interface that is molded into the rotary drive shaft, minimizes the axial length required for the drive coupling. Reducing the drive coupling length reduces the overall length of probe 32.

Figure 7:
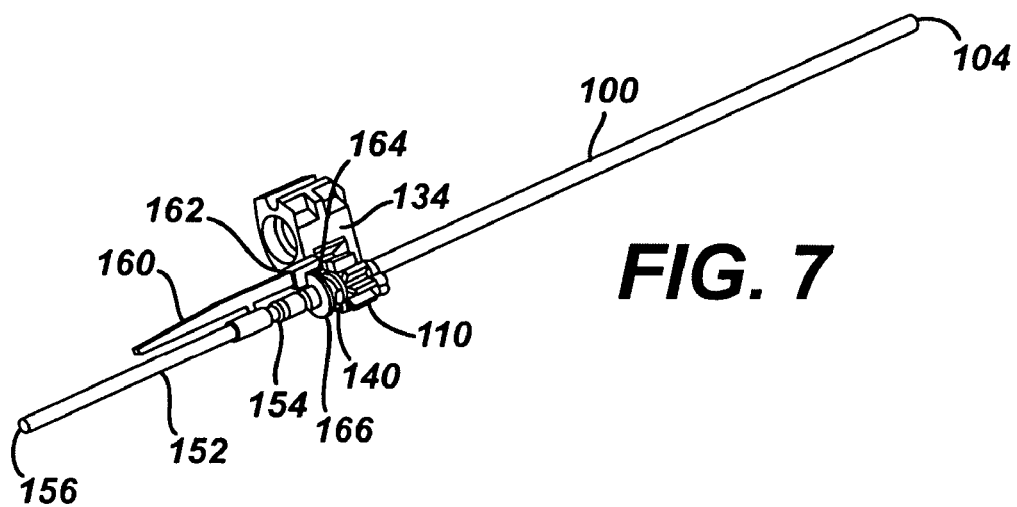
FIG. 7 is an isometric view of an alternative embodiment for the cutter and drive carriage in which the cutter is removable from the probe assembly.
Figure 8:
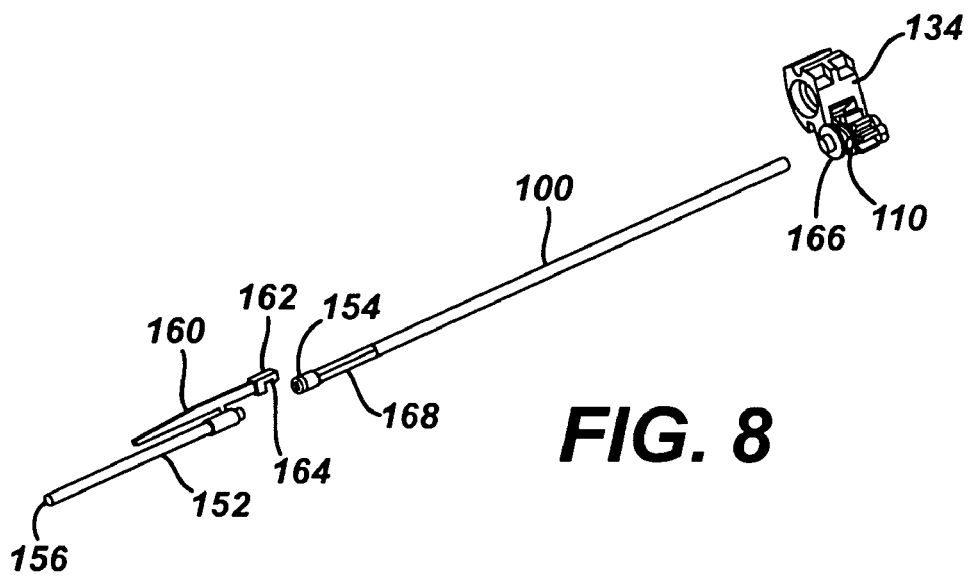
FIG. 8 is an isometric view similar to FIG. 7, illustrating the cutter and rear tube disengaged from the carriage and rotary drive gear for removal from the probe assembly.

FIGS. 7 and 8 illustrate an alternative embodiment for the invention, in which cutter 100 and rear tube 152 are releasable from probe assembly 32 such that the cutter 100 can be repeatedly removed and re-inserted into the probe assembly 32 without disassembling the probe assembly 32. Removal (either partial or complete removal) of the cutter 100 can be advantageous, such as where the cutter 100 is formed of metal and the imaging device employed with the probe 32 is a Magnetic Resonance Imaging (MRI) device. In FIGS. 7 and 8, the proximal portion of rear tube 152 is not shown.

In the embodiment shown in FIGS. 7 and 8, cutter 100 and rear tube 152 can be joined at a seal 154 just proximal of cutter gear 110, such that the cutter is capable of rotating relative to the rear tube 152 (which can be supported to not rotate). A cutter release lever 160 can be supported on and can protrude from rear tube 152. Release lever 160 as shown includes an end 162 extending distally towards carriage 134. A lateral slot 164 in end 162 is shaped and sized to engage a feature associated with carriage 134, such as a disk feature 166 which can be securely attached to a proximal hook extension 140 of carriage 134. While slot 164 engages disk 166, cutter 100 and rear tube 152 translate together with carriage 134. A spline features 168 located near the proximal end of cutter 100 can be employed to engage with a complimenting spline feature on the internal diameter of cutter gear 110 to insure the cutter 100 and cutter gear 110 rotate together.

To remove cutter 100 and tube 152 from probe assembly 32, such as for imaging prior to a cutting cycle, the proximal end of release lever 160 is squeezed in the direction of tube 152. The squeezing action unlatches slot 164 from disk 166, releasing cutter 100 and tube 152 from both the carriage 134 and the cutter gear 110. As shown in FIG. 8, after tube 152 and cutter 100 are released, the tube and cutter may be pulled proximally through the cutter gear bore and out the proximal end of probe assembly 32. To reinsert cutter 100 and tube 152, the tube and cutter are connected at seal 154, and the combination is inserted through the proximal end of probe assembly 32 so that the cutter again extends through the cutter gear bore and union sleeve bore 94 into cannula 82.

Cutter 100 and tube 152 are pushed distally through probe assembly 32 until slot 164 of end 162 again latches onto disk 166.

The cutter 100 may be repeatedly removed from and reinserted into the probe assembly 32 through an opening in the proximal end of the probe assembly 32. The tissue receiving port 86 can be positioned in tissue to be sampled, the cutter 100 can be removed from the probe assembly 32, the biopsy site can be imaged, such as by using MRI, the cutter can be inserted into the probe assembly 32, and the tissue received in the side tissue port 86 can be severed with the cutter 100. The step of removing the cutter from the probe assembly can be performed before or after the tissue port 86 is positioned within the tissue to be sampled. Additionally, the cutter can be removed after a tissue sample is severed, either before or after the needle 80 is removed from tissue.

Figure 9A:
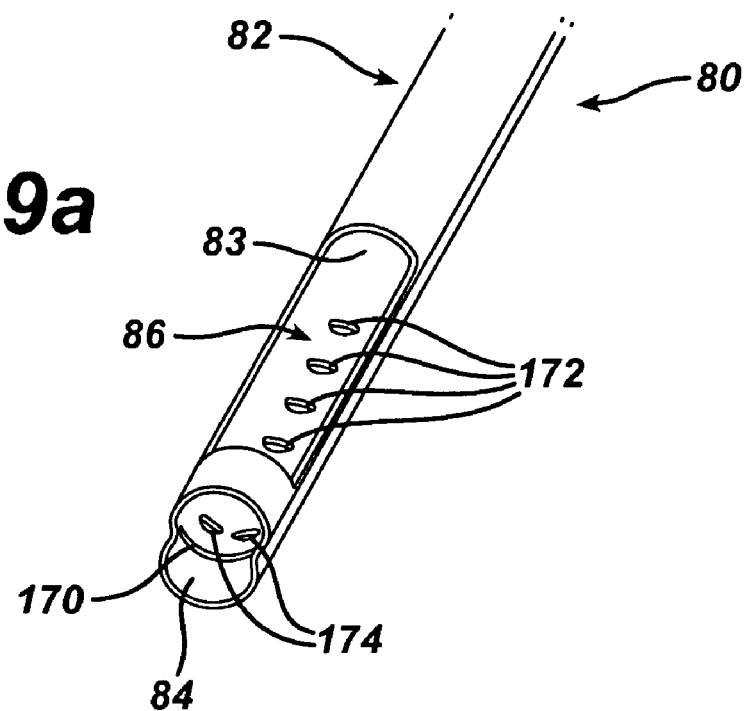
FIG. 9a is an isometric view of the distal end of the biopsy needle illustrating the needle lumen and divider in greater detail.
Figure 9B:
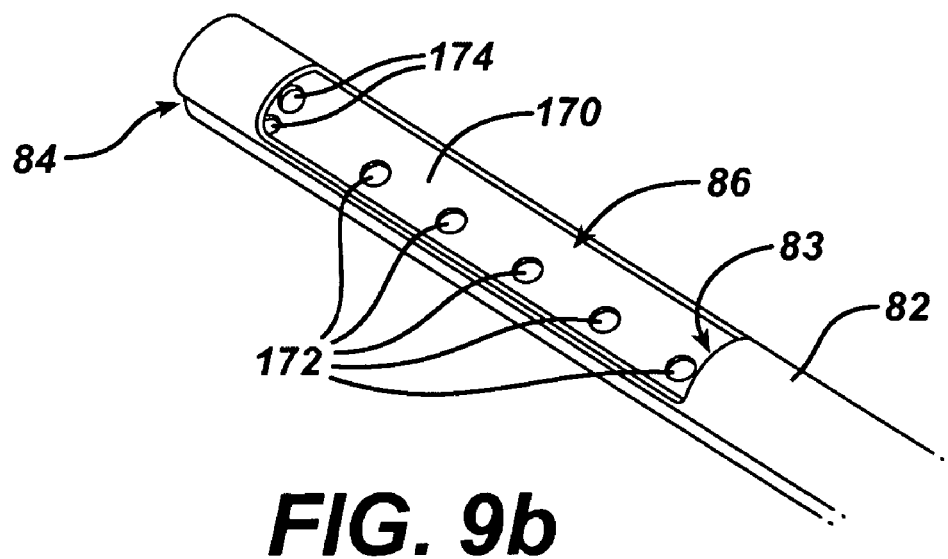
FIG. 9b is a top isometric view of the distal portion of the biopsy needle illustrating the side tissue receiving port in greater detail.

As shown in FIGS. 9a and 9b, a divider 170 may be inserted in the distal end of cannula 82 to separate the interior of needle 80 into upper and lower lumens 83/84. In the embodiment shown in FIGS. 9a and 9b, divider 170 extends axially through cannula 82 to a point just proximal of tissue receiving port 86. The proximal end of divider 170 can coincide with the proximal most position of cutter 100 so that the cutter and divider combine to separate the upper and lower lumens. Alternatively, divider 170 could extend axially through the full length of needle 80. As shown in FIG. 9a, divider 170 can comprise a curved surface that conforms closely to the outer circumference of cutter 100 to enable the cutter to slide along the surface of the divider as the cutter translates within cannula 82. A plurality of fluid passageway holes 172 can be formed in divider 170 beneath tissue receiving port 86 (spaced approximately 180 degrees from the port 86). Fluid passageways 172 can be sized to permit fluid communication between lumens 83 and 84 (and tissue receiving port 86), while preventing excised tissue portions from passing into the lumen. Divider 170 can also include one or more fluid passageways 174 distal of the tissue receiving port 86 through which compressed gas (e.g. air) or liquid (e.g. saline) can be provided to the distal face of a tissue sample located within the cutter lumen 104 while the cutter 100 is in its distal most position closing off the tissue receiving port 86. With cutter 100 in the distal most position and closing off the tissue receiving port 86, tissue samples can be pushed through the cutter 100 without exposing tissue surrounding the cannula 82 to the fluid. Divider 170 may be formed of the same material as cannula 82, and the longitudinal edge of the divider may be welded or otherwise permanently affixed to the inner diameter of the cannula.

Figure 10:
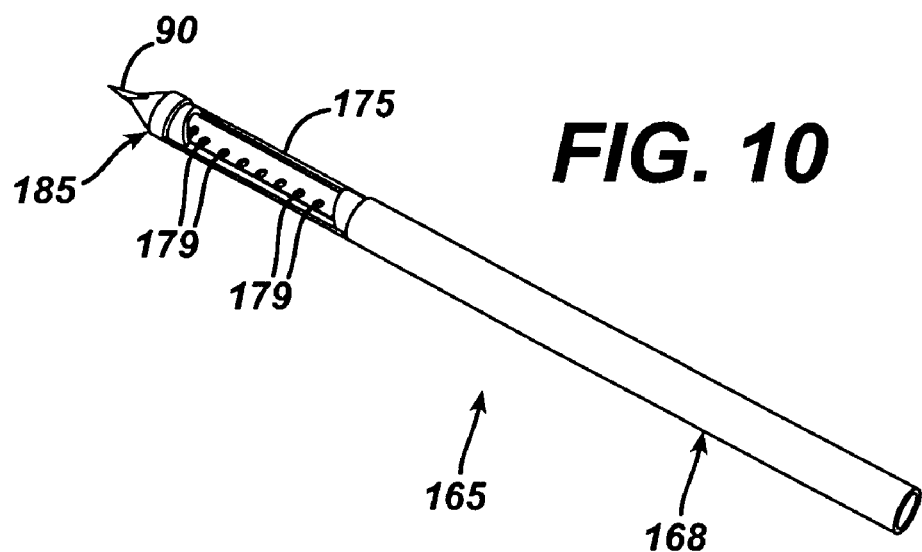
FIG. 10 is an isometric view of an alternative embodiment for the biopsy needle.
Figure 11:
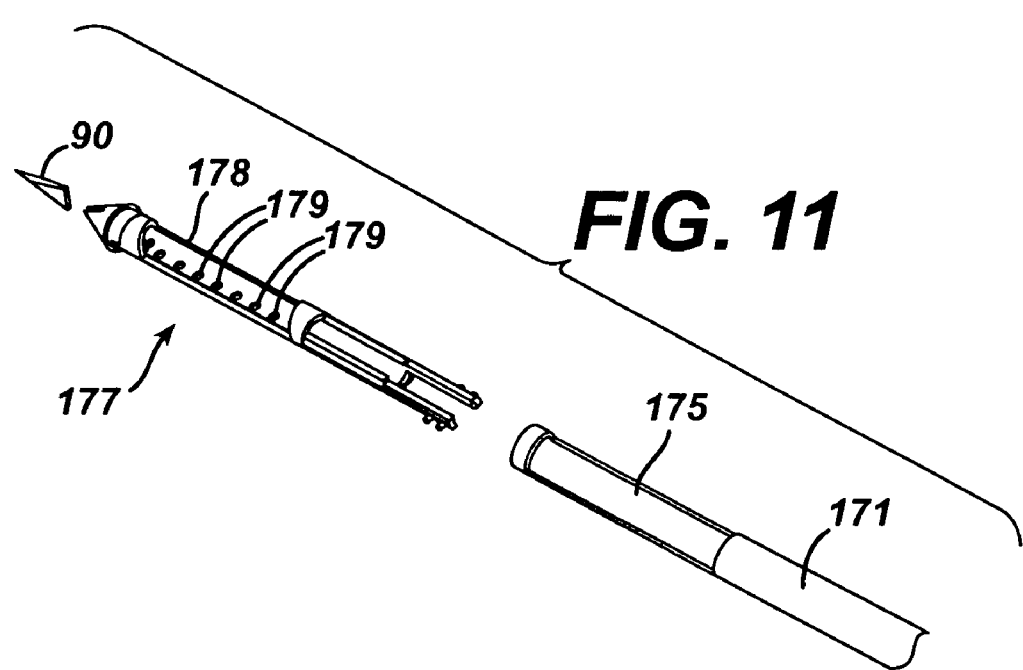
FIG. 11 is an exploded isometric view of the biopsy needle shown in FIG. 10.

FIGS. 10 and 11 illustrate an alternative embodiment for a biopsy needle suitable for use with a probe assembly 32. The needle, designated by numeral 165, can be assembled from an aperture component, a tissue piercing component, and a tube component. In this embodiment, tube component 168 comprises a cannula 171 having a lumen 173 extending there through, and a tissue receiving aperture 175 adjacent the distal end of the tube. The aperture component 177 comprises an aperture 178 and fluid passageways 179. The tissue piercing component component 90 can be insert molded into the aperture component or mechanically secured to it, such as with adhesive or other suitable bonding means.

Figure 12:
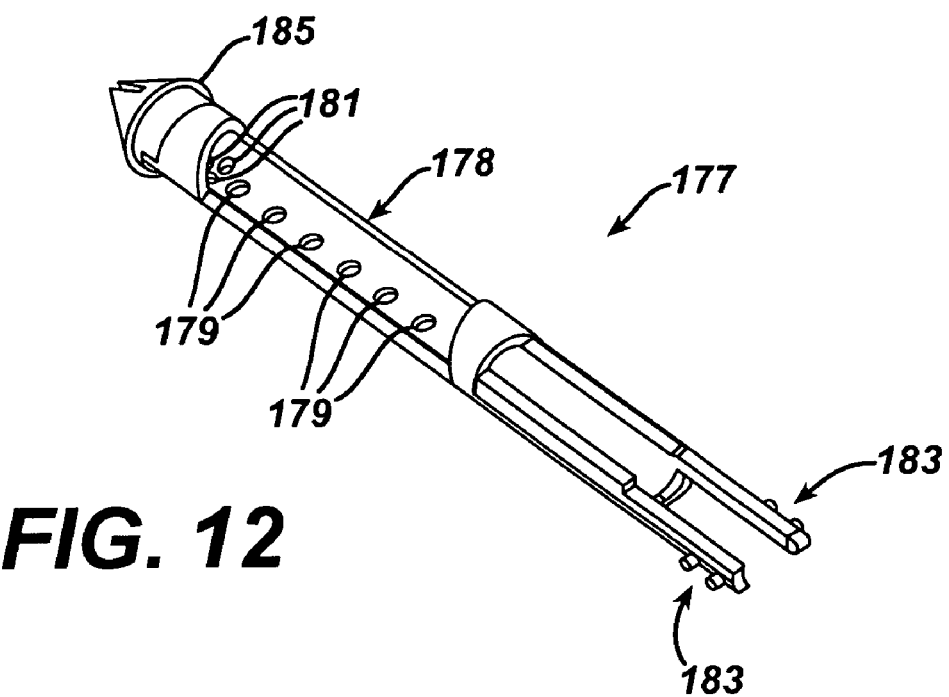
FIG. 12 is a more detailed top isometric view of the aperture component shown in FIG. 11.
Figure 13:
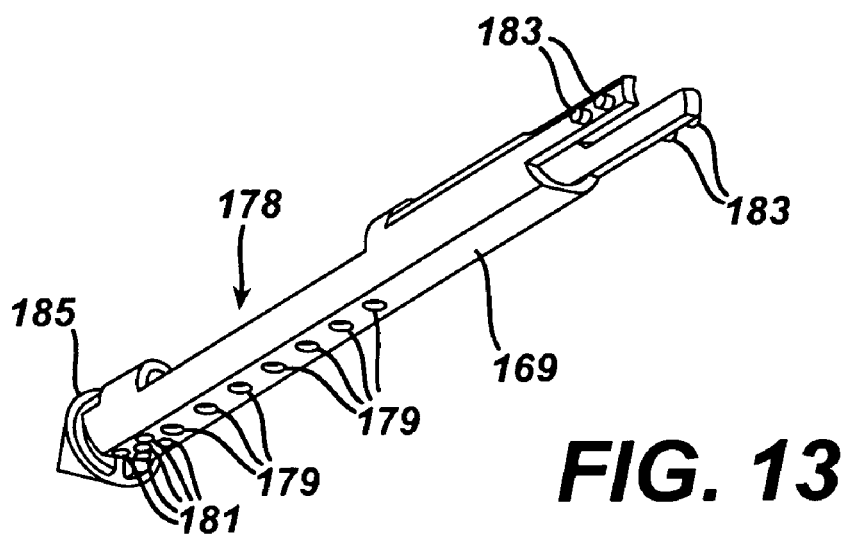
FIG. 13 is a more detailed bottom isometric view of the aperture component shown in FIG. 11.

As shown in greater detail in FIGS. 12 and 13, aperture component 177 can have a semi-tubular shape with an upper opening 178 of substantially the same length as tissue receiving aperture 175. Opening 178 aligns with tissue receiving aperture 175 when the two components 168, 177 are assembled together. A plurality of fluid passageways 179 are formed in a lower surface 169 of aperture component 177 beneath opening 178. Lower surface 169 can provide a divider for providing a lower lumen when needle 165 is assembled. One or more fluid passageways 181 can be provided distal of opening 178 so as to be distal of tissue receiving aperture 175 when the needle components are assembled together. Passageways 179 and 181 provide flow communication for compressed fluid (e.g. air and/or saline) from the lower lumen to the upper lumen when needle components 168, 177 are assembled together. A pair of engagement bosses 183 can be provided and can extend from the proximal end of aperture component 177 for attaching the aperture component to tube component 168. To assemble needle 165, aperture component 177 is inserted through the distal end of cannula 171 until bosses 183 engage complimentary grooves or holes on the inner diameter of the tube component 168. The engagement between the bosses and grooves locks aperture component 177 within tube component 168. In addition, when needle 165 is assembled into probe assembly 32, the portion of the cutter 100 which extends distally beyond bosses 183 in tube component 168 can further prevent the aperture component 177 from disengaging form the tube component 168. A circumferential lip 185 can be provided on the aperture component 177. The lip 185 can provide a seating surface for the distal end of tube component 168 when the aperture component is assembled with the tube component.

Figure 14:
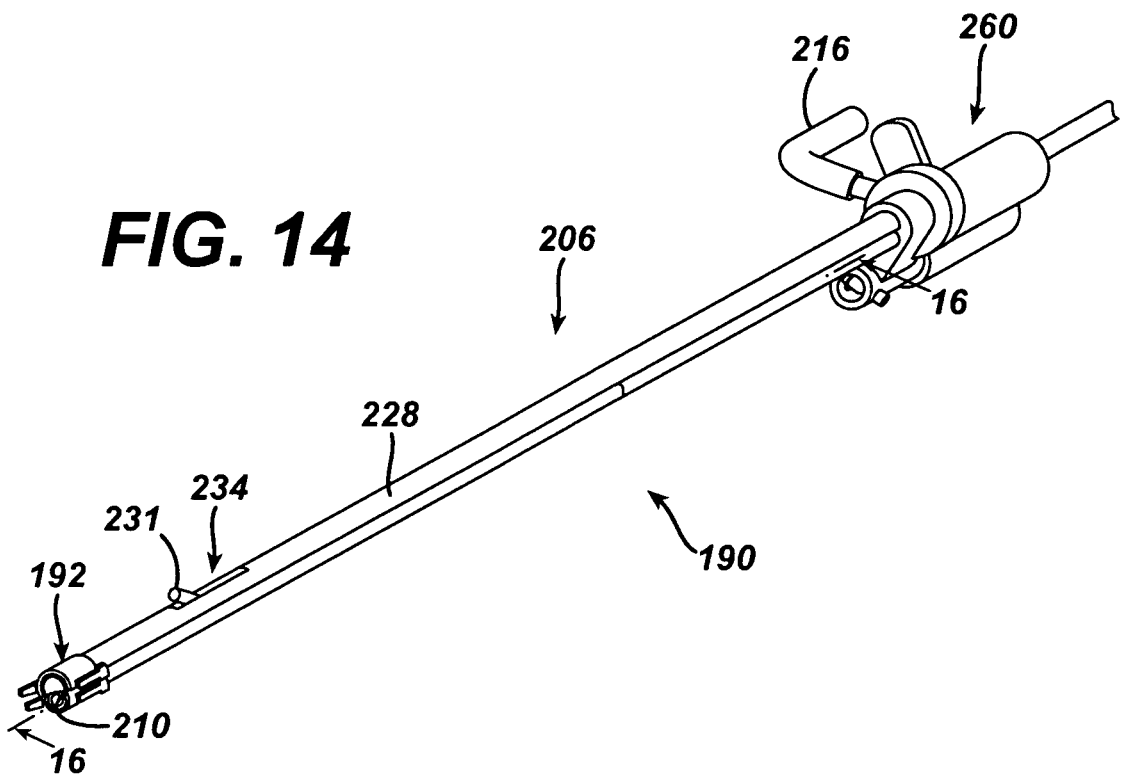
FIG. 14 is an isometric view of a serial tissue stacking assembly.

Referring again to FIG. 5, once a tissue sample enters the lumen 104 of cutter 100, the axial vacuum force 180 can serve to pull the sample proximally through the cutter 100 to be directed from probe assembly 32 into tissue storage assembly 52. In a first embodiment, tissue storage assembly 52 comprises a serial tissue stacking assembly 190, such as is shown in FIG. 14. In serial tissue stacking assembly 190, multiple tissue samples are stacked one behind the next in an end to end configuration, such as in a flexible tube. The samples may be removed individually from the tube and examined in real-time during the procedure or, alternatively, left in the tube until the end of the procedure and removed all at once. The distal end of serial tissue assembly 190 can be detachably connected via dual connection mechanisms to probe assembly 32 (so that the serial tissue storage assembly 190 is releasable from the probe assembly), while the proximal end of the assembly 190 can be detachably connected via tube 42 to a vacuum source, such as vacuum source 36 shown in FIG. 1.

Figure 15A:
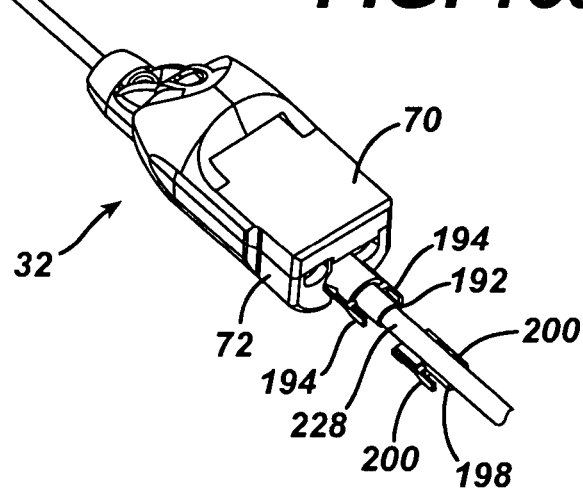
FIG. 15a is an isometric view of the probe assembly of FIG. 2 and the distal end of the serial tissue stacking assembly of FIG. 14, illustrating the probe assembly attached to the serial tissue storing assembly.
Figure 15B:
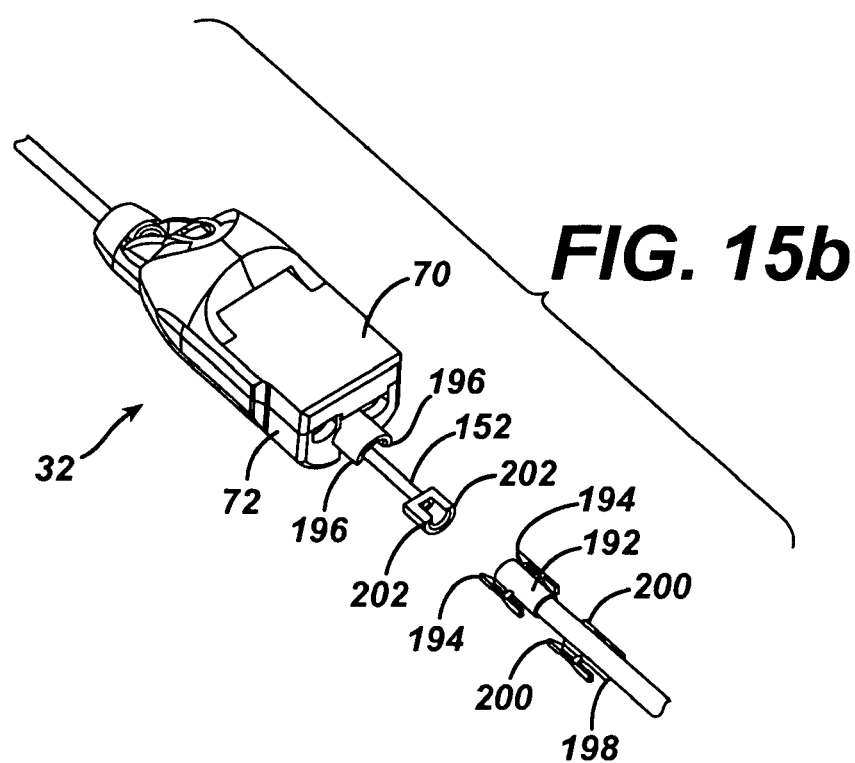
FIG. 15b is an isometric view similar to FIG. 15a, showing connectors for attaching the serial tissue storing assembly to the probe assembly.

In the embodiment shown in FIGS. 15a and 15b, an upper connector 192 at the distal end of serial tissue assembly 190 includes a pair of snap fasteners 194. Fasteners 194 engage a pair of fastener engaging features 196 that are disposed at the proximal end of the probe assembly, such as a pair of notches that can be formed in a portion of the proximal end of probe lower shell 72. When fasteners 194 are engaged with features 196, as shown in FIG. 15a, the upper portion of serial tissue assembly 190 is attached to the probe housing.

A second, lower connecter 198, also at the distal end of serial tissue assembly 190, can include a similar pair of snap fasteners 200. Lower snap fasteners 200 engage a mating pair of features 202 on the proximal end of the rear tube 152 that is shown extending from a proximal opening in probe assembly 32 in FIG. 15b. The distal end of rear tube 152 can be joined to carriage 134 as shown in FIG. 8. When lower snap fasteners 200 engage notches 202, as shown in FIG. 15b, the lower portion of serial tissue assembly 190 moves distally and proximally with the translation of drive carriage 134. When both upper connector 192 and lower connector 198 are attached to probe assembly 32, the lower portion of serial tissue assembly 190 will translate relative to the fixed upper portion of the assembly during the cutting cycle. To detach serial tissue assembly 190 from probe assembly 32, each of the pairs of snap fasteners 194, 200 are pushed inwardly at the distal ends to disengage the forward tips of the fasteners from the corresponding notches 196, 202. After the fasteners are disengaged, serial tissue assembly 190 may be separated from probe assembly 32.

Figure 16:
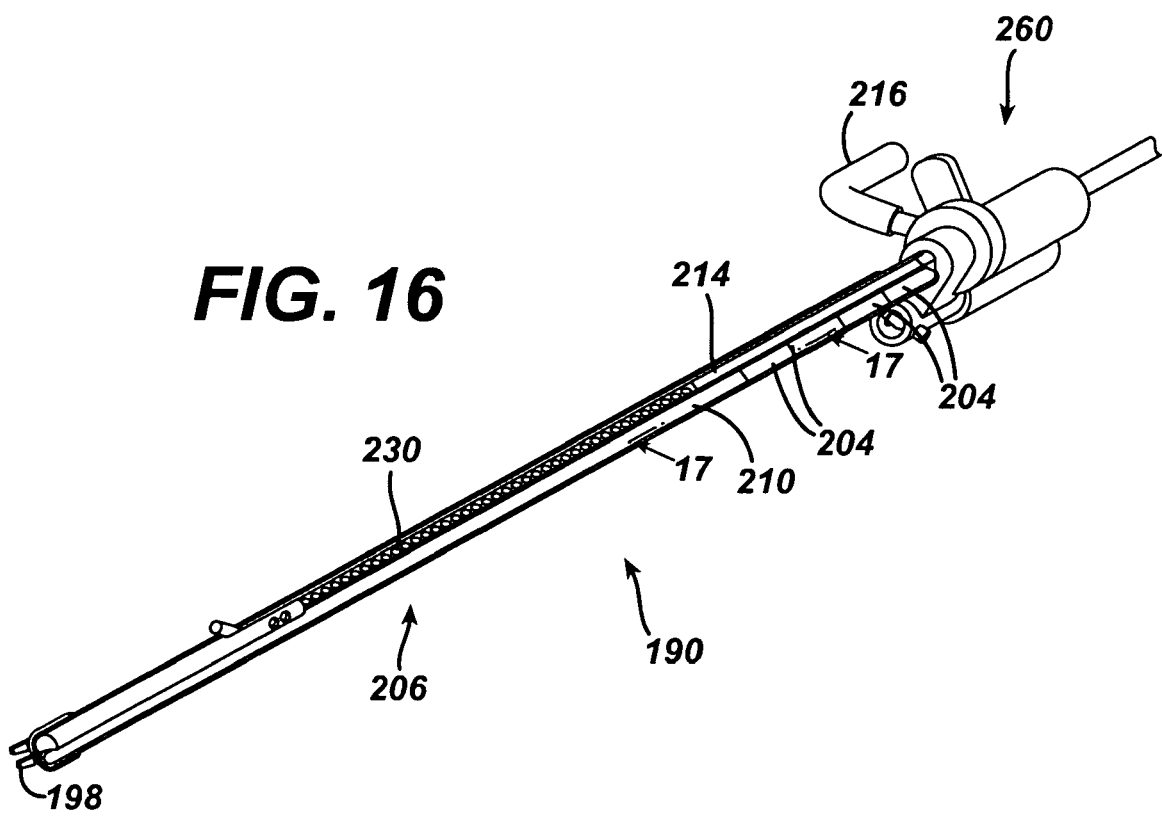
FIG. 16 is a side cross-sectional view taken along line 16—16 of the serial tissue stacking assembly of FIG. 14.

As shown in FIGS. 14 and 16, serial tissue assembly 190 includes a sample storage tube 206 having dual lumens extending axially therethrough. The dual lumens can be generally parallel. Tube 206 may be comprised of polyvinyl chloride or another similar type of flexible, water insoluble material. Using a clear material for storage tube 206, such as polyvinyl chloride, enables the stacked tissue samples to be visible from outside the tube.

Tube 206 can include a longitudinally extending center wall divider for separating the two lumens. Tube 206 can comprise a first lumen, such as stacking lumen 210, for transferring and storing tissue samples 204 that have been aspirated to the assembly through cutter lumen 104. Tissue stacking lumen 210 can be detachably connected to the proximal end of rear tube 152 by lower connector 198. When fasteners 200 engage features 202, as described above, tissue stacking lumen 210 can be axially aligned with rear tube lumen 156 to provide a continuous, unobstructed passageway for the movement of tissue samples 204 from tissue receiving port 86 into the tissue lumen stacking lumen 210.

As tissue samples 204 enter tissue stacking lumen 210, the samples stack serially one behind the next within the lumen, in end to end configuration, as shown in FIG. 16, so that the order of the samples (the order in which the samples are obtained from the biopsy site) is maintained while the samples are stored in tissue stacking lumen 210. A tissue stop can be located within the tissue retrieval mechanism 260 at the proximal end of tissue lumen 210 to prevent the first or earliest sample from translating completely through the tissue lumen and into vacuum system 36. The tube 206 can comprise a second lumen, tissue stacking vacuum lumen 214, for providing a flow communication path for vacuum through rear tube 152 and cutter 100 so that severed tissue samples 204 can be drawn through cutter 100 and rear tube 152 into tissue stacking lumen 210. The proximal end of tissue stacking vacuum lumen 214 can be detachably connected to vacuum source 36 through a lateral attachment port 216.

Figure 17:
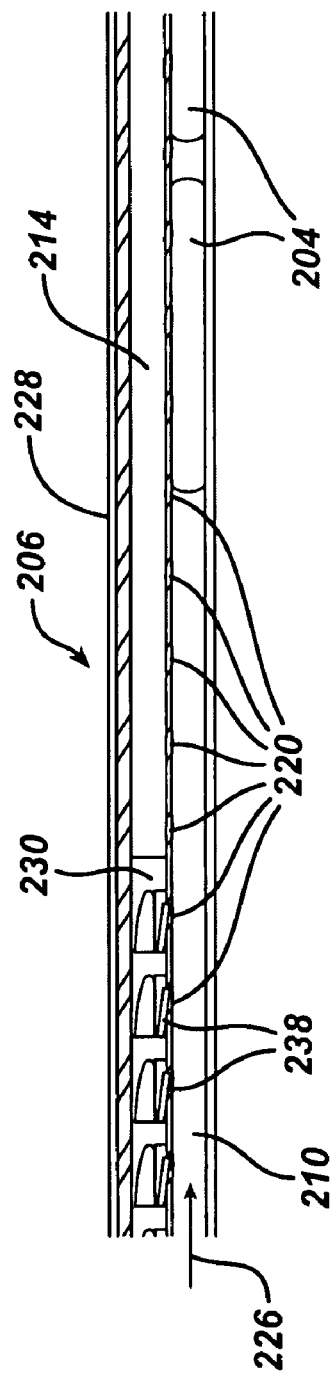
FIG. 17 is a side cross-sectional view taken along line 17—17 of FIG. 16, illustrating the vacuum communication holes of the serial tissue stacking tube in greater detail.

As shown in greater detail in FIG. 17, a plurality of small holes 220 can be provided in the center wall divider of tube 206 between lumen 214 and lumen 210 to provide flow communication between the lumens. Holes 220 enable vacuum from source 36 to be communicated from lumen 214 into lumen 210, to provide vacuum in lumen 104 of cutter 100. Holes 220 are preferably spaced along the longitudinal axis of tube 206 and separated by a distance in the range of 0.1 to 4 centimeters. Holes 220 may be oriented at an angle relative to the longitudinal axis of tube 206. The angle in holes 220 can function as a mechanical diode, in that the edge of the holes 220 opening into lumen 210 can aid in preventing motion of tissue samples in a distal direction, while permitting tissue samples to move proximally in lumen 210 under vacuum force provided by vacuum source 36. A tissue sample will continue to slide proximally through the lumen 210 until the sample contacts either the tissue stop within the tissue retrieval mechanism 260 or a preceding tissue sample.

Vacuum holes 220 may be formed between lumens 210, 214 by boring into the upper surface of tube 206 with the sharpened tip of a drill or other appropriate instrument. The tip of the drill bit or other boring instrument can be directed to pass through vacuum lumen 214 to penetrate the center wall of tube 206 that separates the two lumens. As shown in FIG. 14, an outer sleeve 228 is securely attached to the surface of tube 206 following the formation of vacuum communication holes 220. Outer sleeve 228 may be attached to tube 206 by an adhesive or other appropriate type of attachment mechanism. Outer sleeve 228 is attached to sample tube 206 over the openings used to form vacuum communication holes 220 to seal the openings, and prevent vacuum from passing out of vacuum lumen 214 through the openings. The distal end of outer sleeve 228 can be formed to extend beyond the distal end of vacuum lumen 214 to connect with upper connector 192. Vacuum lumen 214 attaches to probe assembly 32 through the connection between outer sleeve 228 and upper connector 192.

As tissue samples 204 are stored in lumen 210, the stack of samples 204 will grow in length distally in lumen 210. The samples 204 will tend to block or otherwise restrict flow communication through vacuum holes 220 as the stack of samples extends distally in lumen 210. In FIG. 16, a translating flexible rod 230 is shown disposed at least partially in lumen 214. Rod 230 can extend axially through lumen 214 to selectively cover or otherwise block at least some of the vacuum holes 220. Rod 230 can then be manipulated, such as by axial movement of rod 230, to selectively expose vacuum holes 220 in the vacuum lumen. For instance, during each cutting cycle, rod 230 can be advanced distally within vacuum lumen 214 to expose or otherwise unblock/open additional vacuum holes 220 as additional samples are stored in lumen 210. The movement of rod 230 maintains a predetermined number of vacuum holes 220 open to provide flow communication between lumens 210 and 214 as additional tissue samples are added to the stack of tissue samples in lumen 210. This can aid in providing a consistent vacuum force in cutter lumen 104 throughout multiple cutting cycles. Initially, flexible rod 230 can be inserted within lumen 214 such that rod 230 is axially offset within lumen 214 so as to cover or otherwise block most, but not all, of the holes 220. For instance, prior to storing any samples in lumen 214, rod 230 can be offset distally within vacuum lumen 214 a distance that is slightly longer than the length of tissue receiving port 86. Offsetting rod 230 distally within lumen 210 ensures an initial set of holes 220 are exposed to communicate axial vacuum force 180 to tissue receiving port 86 when cutter 100 is in the fully proximal position prior to tissue sampling. The axial vacuum force communicated through the exposed holes 220 aids in prolapsing tissue into receiving port 86 prior to cutting, as well as pulling the tissue sample proximally into tissue lumen 210 after cutting. As a tissue sample is drawn into and stacked within tissue lumen 210, the tissue sample blocks the previously exposed vacuum holes 220, preventing vacuum from passing into the tissue lumen. Rod 230 can be selectively moved a predetermined distance distally that is slightly longer than the length of tissue receiving port 86 to expose additional vacuum holes 220 immediately distal of the most recently acquired tissue sample. Rod 230 can be adapted to be automatically advanced distally by the translation of drive carriage 134 within probe assembly 32, as described further below. The newly exposed vacuum holes 220 continue the communication of vacuum force 180 into tissue lumen 210 for the next cutting cycle.

Rod 230 can be formed of a fluoropolymer resin material such as Teflon® or other suitable flexible material having a low coefficient of friction. Rod 230 can be sized and shaped to conform closely to the inner diameter of vacuum lumen 214. The close fit between rod 230 and vacuum lumen 214, as well as the low friction properties of the rod, enable the rod to translate easily within the vacuum lumen without any loss of vacuum force through the distal end of the lumen.

Figure 18:
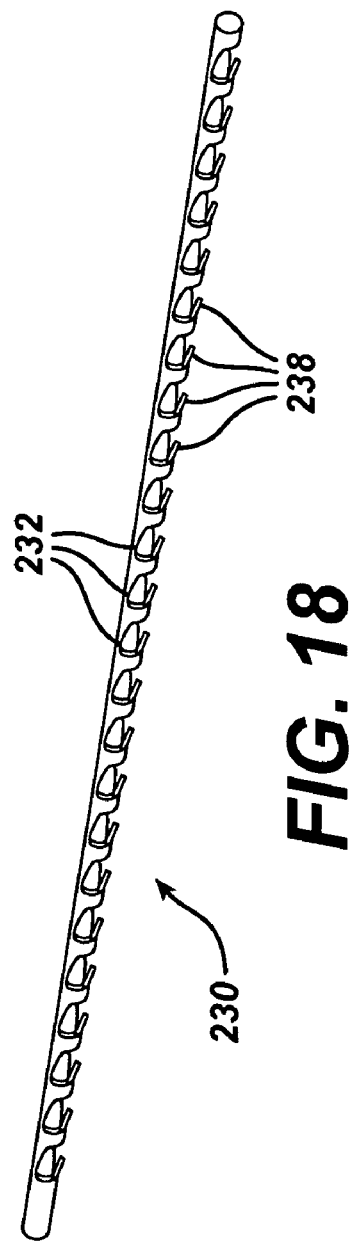
FIG. 18 is an isometric view of the translating flexible rod.

The distal end 231 of rod 230 extends outside of vacuum lumen 214 through an opening 234 in outer sleeve 228. As rod 230 is advanced distally, the rod moves further out of vacuum lumen 214 through opening 234. The flexibility of rod 230 allows the rod to flex out of opening 234 in outer sleeve 228 as the rod is continually advanced distally, enabling substantially the entire rod to be translated out of vacuum lumen 214 over the course of multiple cutting cycles. As shown in greater detail in FIG. 18, rod 230 can include a plurality of side ratchet teeth 232 spaced longitudinally substantially along the length of the rod. Teeth 232 provide a mechanism to grip and advance rod 230 through vacuum lumen 214. Rod 230 can also include a plurality of bottom ratchet teeth 238.

Figure 19:
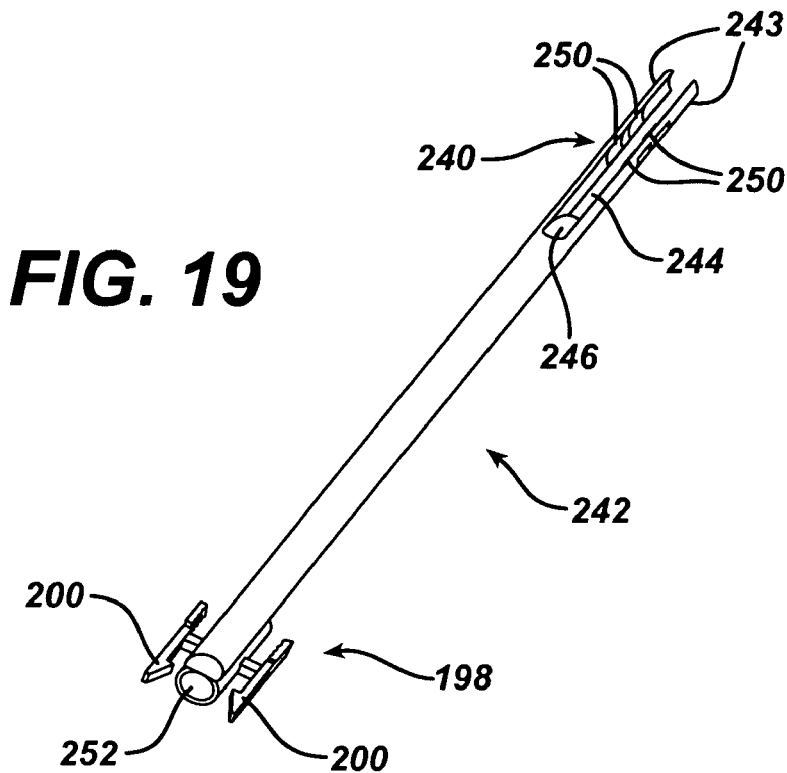
FIG. 19 is an isometric view showing the reciprocating member and lower connector in greater detail.

Rod 230 can be advanced distally within vacuum lumen 214 by the interaction between teeth 232 and a pawl-type latching mechanism 240 on a reciprocating member 242, which is shown in greater detail in FIG. 19. Reciprocating member 242 can be supported on lower connector 198 and reciprocates as cutter 100 is advanced and retracted. Reciprocating member 242 can have a bifurcated proximal end with proximally extending portions 243 separated by an axially extending slot 244. A ramped surface 246 can be formed between portions 243 at a distal end of slot 244. Ramped surface 246 can serve to deflect the distal end 231 of rod 230 through opening 234 and alongside the outer surface of tube 206 as the rod is ratcheted out of vacuum lumen 214. Unidirectional engagement pawls 250 can be formed to extend from the sides of portions 243 facing slot 244 to engage side ratchet teeth 232 on rod 230 as the rod extends through the groove. The engagement between pawls 250 and ratchet teeth 232 advances rod 230 distally through vacuum lumen 214.

The distal end of reciprocating member 242 can be fixed to lower connector 198 for translation along with the lower connector 198, carriage 134, and cutter 100 during each cutting cycle. As drive carriage 134 advances distally at the beginning of a cutting cycle to move cutter 100 into receiving port 86, reciprocating member 242 also advances distally. As reciprocating member 242 advances, pawls 250 in groove 244 engage side teeth 232 on rod 230 in lumen 214 to pull the rod distally with the reciprocating member. As rod 230 moves distally within lumen 214, additional vacuum holes 220 are exposed. As the direction of carriage 134 reverses, and cutter 100 retracts from receiving port 86, reciprocating member 242 moves in a proximal direction relative to the fixed vacuum lumen 214. As reciprocating member 242 retracts proximally, unidirectional bottom ratchet teeth 238 located on the bottom side of flexible rod 230 engage vacuum holes 220 within vacuum lumen 214 as shown in FIG. 17. The engagement between the ratchet teeth and holes 220 prevents rod 230 from moving proximally within vacuum lumen 214. As pawls 250 move proximally relative to rod 230, the pawls engage the next proximal set of ratchet teeth 232 on rod 230. This engagement with the next set of ratchet teeth 232 causes rod 230 to again advance distally when drive carriage 134 advances distally during the next cutting cycle to expose additional vacuum communication holes 220. In the event that the carriage and cutter assembly is advanced and retracted without the probe assembly 32 in tissue, resulting in the flexible rod 230 advanced too far distally relative to the tissue samples 204; the flexible rod 230 can be rotated a fraction of a turn about its longitudinal axis to disengage ratchet teeth 232 and 238 allowing the flexible rod 230 to be repositioned proximally within the vacuum lumen 214.

In an alternative embodiment not shown, flexible rod 230 could be advanced distally within vacuum lumen 214 as drive carriage 134 is retracted proximally following the cutting of tissue. In this embodiment, a reversing mechanism such as, for example, a cable extending 180° degrees around a pulley, could be utilized so that as the drive carriage retracts the cable pulls the flexible rod distally.

As shown in FIG. 19, lower connector 198 includes an axially-extending bore 252 for connecting the tissue lumen portion of sample tube 206 to rear tube 152. When serial tissue assembly 190 is connected to probe assembly 32 by lower connector 198, tissue lumen 210, bore 252, and rear tube lumen 156 are aligned generally coaxially to provide an unobstructed passageway for the aspiration of tissue samples from cutter 110 and rear tube 152 to lumen 210.

Figure 20:
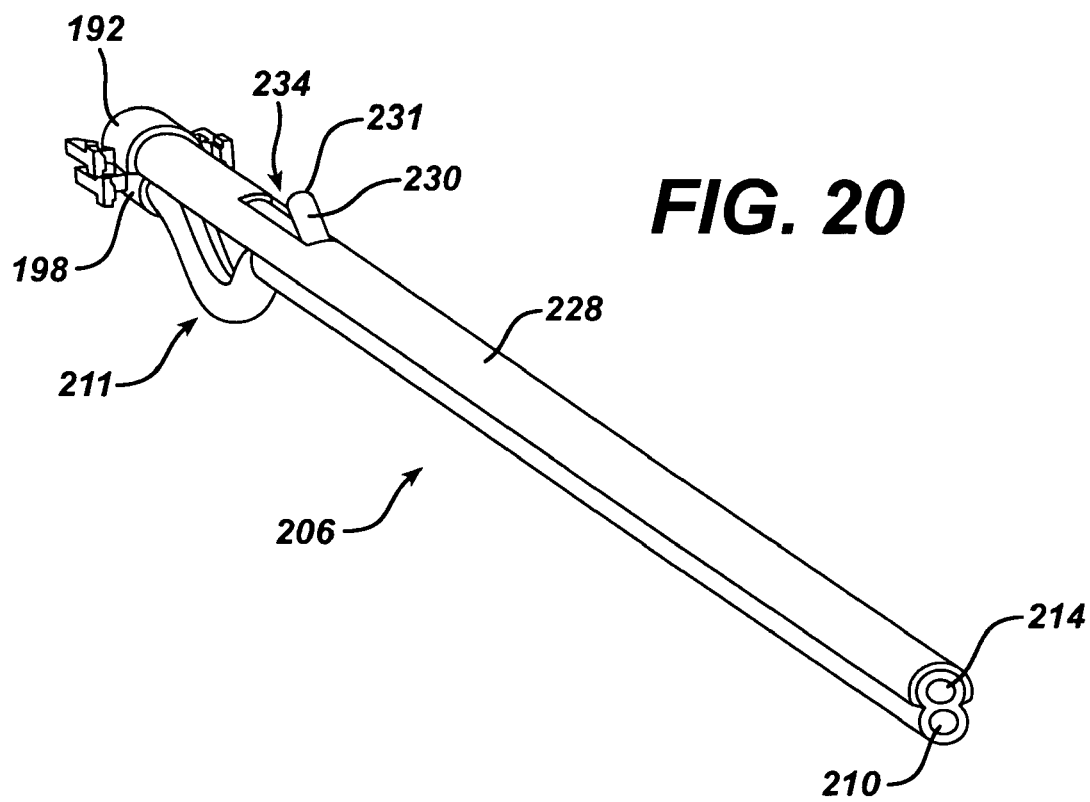
FIG. 20 is an isometric view showing the probe connectors and distal end of the tissue sample storage tube in greater detail.

FIG. 20 illustrates in greater detail connectors 192, 198 and lumens 210, 214. As shown in FIG. 20, vacuum lumen 214 can be attached to fixed upper connector 192 by outer sleeve 228. Vacuum lumen 214 thus remains fixed in position within serial tissue assembly 190 throughout the cutting cycle. Tissue lumen 210 extends distally into bore 252 of lower connector 198. At least a distal portion of tissue lumen 210 will translate along with lower connector 198 and drive carriage 134 during each cutting cycle. As drive carriage 134 and lower connector 198 translates proximally, a distal portion 211 of the sample tube including the distal portion of tissue lumen 210 flexes or otherwise deforms downward, enabling the distal end of the tissue lumen to translate along with lower connector 198 and reciprocating member 242, while vacuum lumen 214 remains fixed in position by outer sleeve 228.

Figure 21:
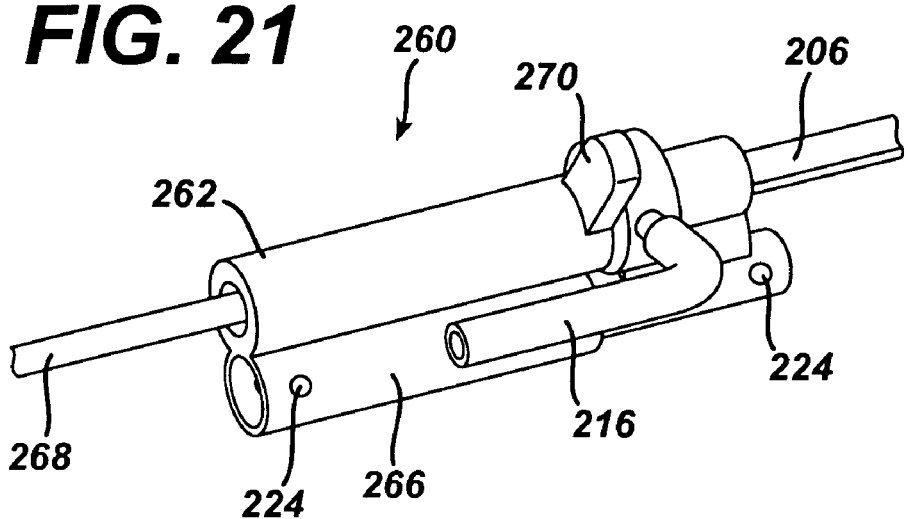
FIG. 21 is a detailed isometric view of the tissue retrieval mechanism shown in FIG. 14, with the outer sleeve of the mechanism in a closed position.
Figure 22:
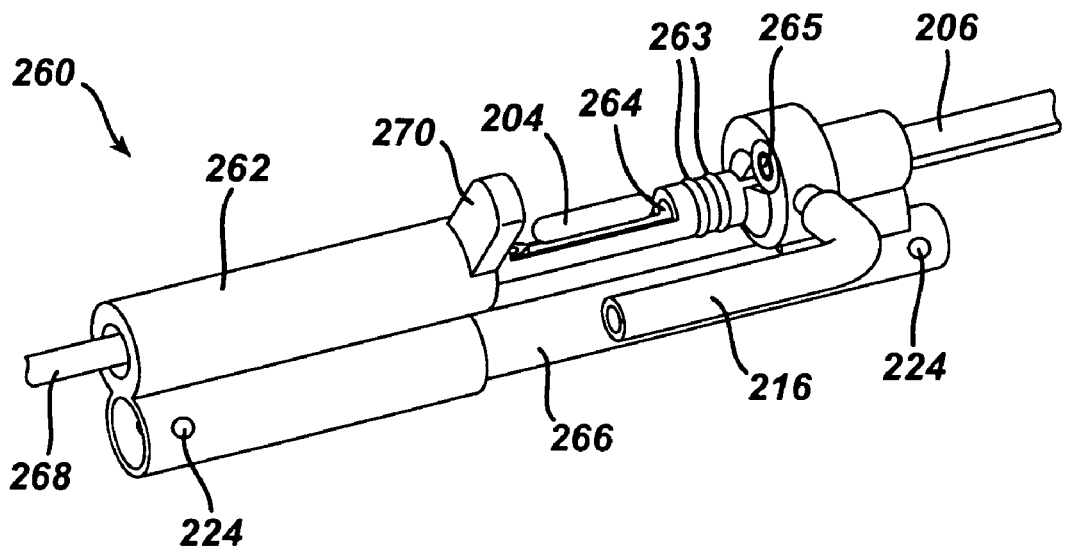
FIG. 22 is a detailed isometric view of the tissue retrieval mechanism of FIG. 21, showing the outer sleeve of the mechanism in an open position.
Figure 23:
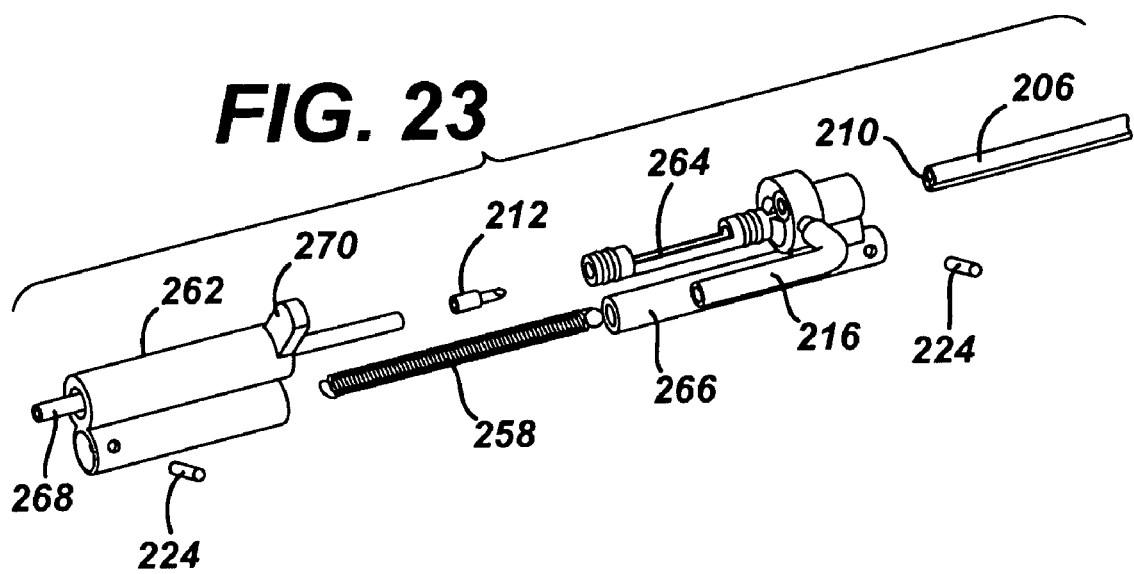
FIG. 23 is an exploded isometric view of the mechanism of FIG. 21.

As shown in FIGS. 14 and 16 a tissue retrieval mechanism 260 may be located at the proximal end of serial tissue assembly 190 for removing samples from the assembly in real-time following each cutting cycle. Tissue retrieval mechanism 260 can be is positioned in relation to sample tube 206 just distal of tissue stop 212 (FIG. 23). As shown in greater detail in FIGS. 21, 22, and 23, tissue retrieval mechanism 260 includes a retractable outer sleeve 262. Outer sleeve 262 is pneumatically sealed by o-rings 263 to maintain vacuum within sample tube 206 during the cutting cycle. To remove a tissue sample from tube 206 following a cutting cycle, outer sleeve 262 is manually rotated or translated out of position using pull-tab 270 to expose the tissue sample in tissue lumen 210. A tissue retrieval window 264 can be formed in tissue lumen 210 beneath outer sleeve 262 to provide access to the tissue sample in the lumen once the outer sleeve is retracted. An air inlet 265 can be located distal of tissue retrieval window 264 to apply air pressure to the distal face of the tissue sample 204 in the window, to prevent distal movement of the sample when outer sleeve 262 is retracted due to a pressure imbalance on tissue sample 204. A lower cylinder 266 on retractable sleeve 262 can house a return spring 258 for biasing the sleeve into the closed, sealed position. Each end of the spring 258 is secured to the retrieval mechanism 260 with pins 224. The proximal end of tissue retrieval assembly 260 can include a vacuum attachment 268 for providing vacuum to tissue lumen 210, such as from vacuum source 36. Vacuum attachment port 216 can also be provided to extend through retrieval mechanism 260 to provide vacuum to lumen 214, such as from vacuum source 36. At the end of a procedure, tissue retrieval assembly 260 may be disconnected from sample tube 206 so that tissue samples may be retrieved from the tube, as will be described in further detail below.

Figure 24:
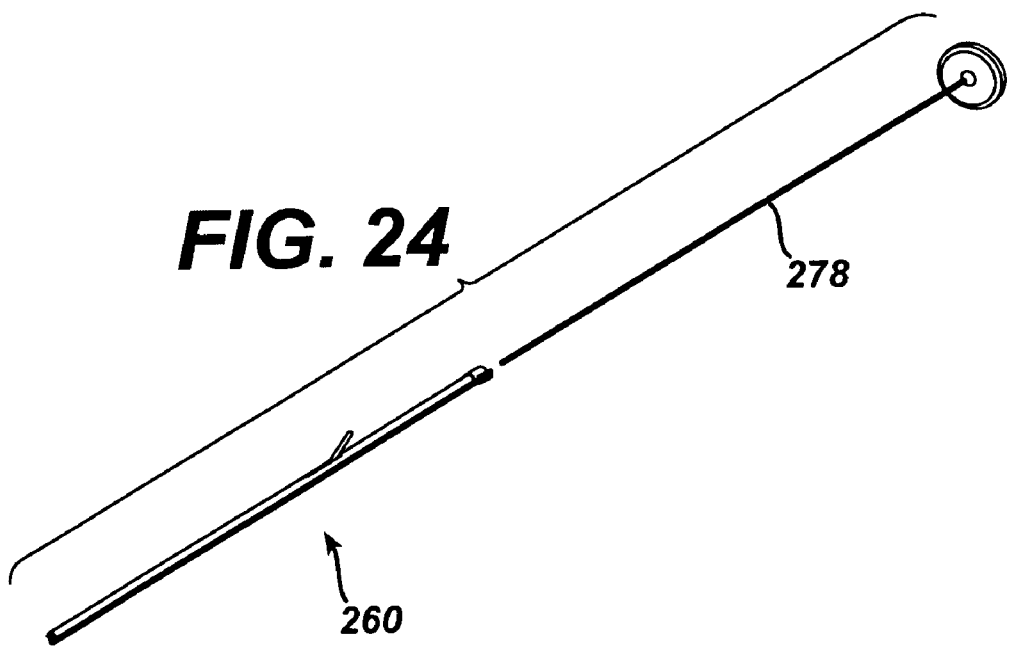
FIG. 24 shows a flexible push rod in the form of a plunger for use in removing samples.
Figure 25:
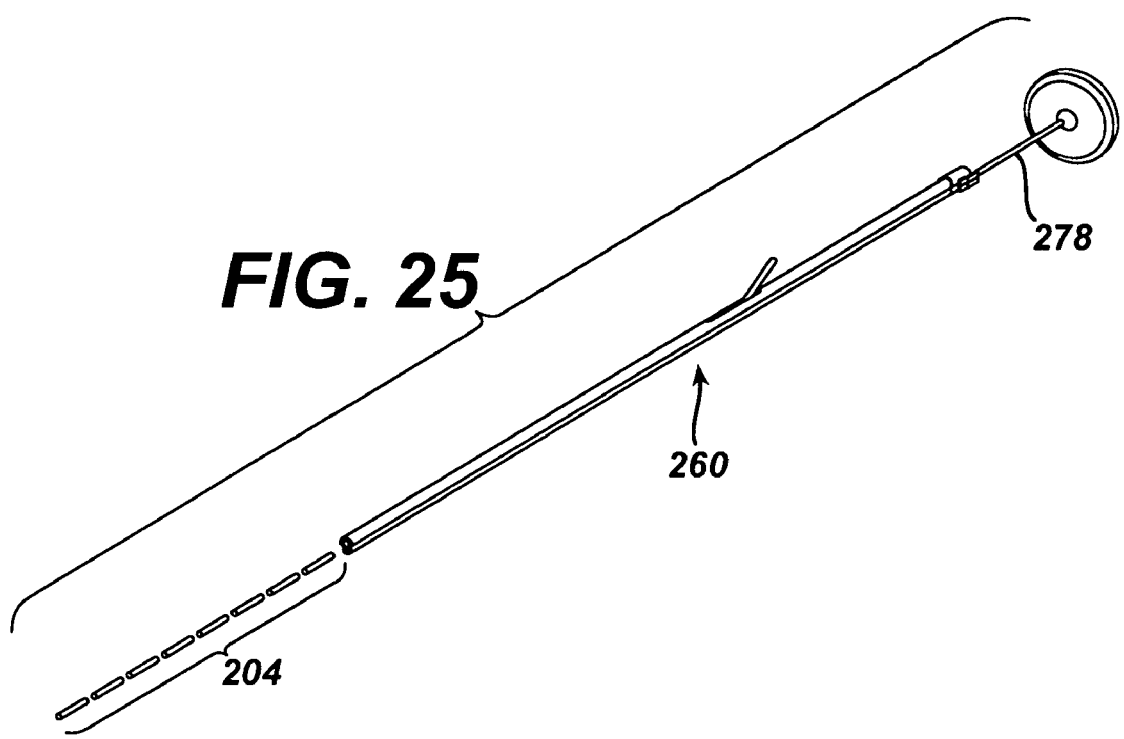
FIG. 25 is an isometric view showing removal of samples.

As an alternative or in combination with real-time sample retrieval through tissue retrieval assembly 260, tissue samples may be retrieved at the end of a procedure by disconnecting sample tube 206 from probe assembly 32 and removing tissue retrieval assembly 260 from the proximal end of tissue lumen 210. After sample tube 206 is disconnected, a sample releasing mechanism such as, for example, the flexible rod such as plunger-like component 278 shown in FIG. 24, may be inserted in one end of tissue lumen 210 and advanced there through to extract the samples from the opposite end of the lumen as shown in FIG. 25. Alternatively, the tissue sample tube may be formed such that vacuum lumen 214 is separable from tissue lumen 210 at the conclusion of the procedure to allow access to the tissue samples stacked within the tissue lumen.

Figure 26A:
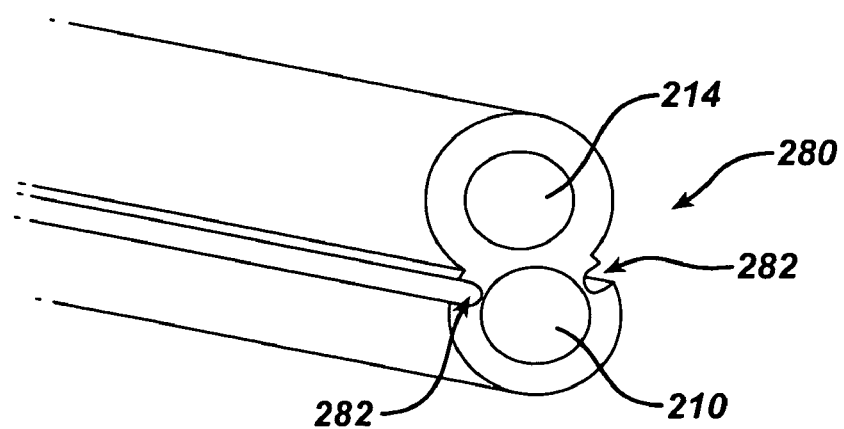
FIG. 26a is a schematic illustration of an embodiment of a separable tissue storage tube.
Figure 26B:
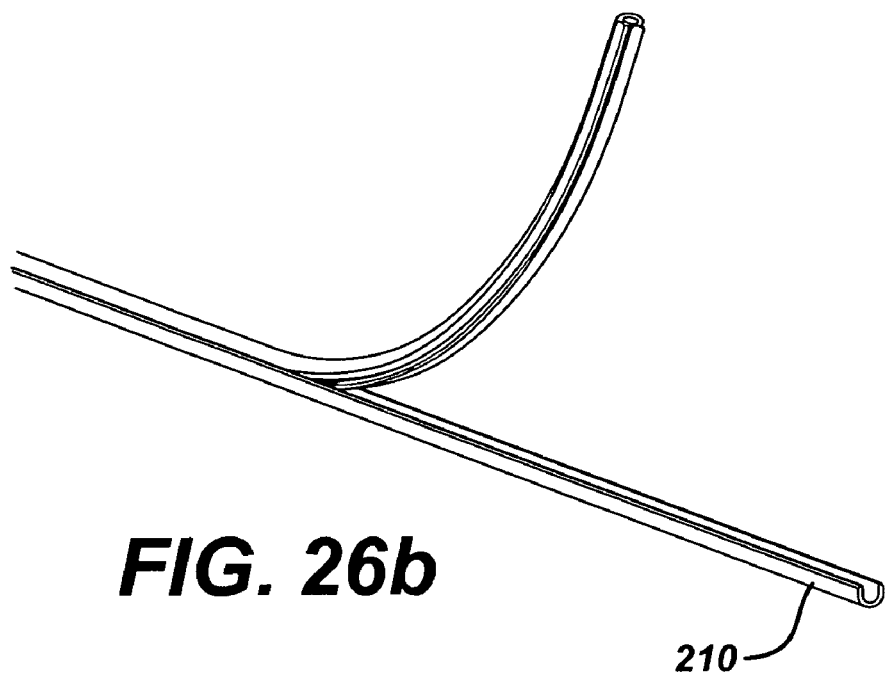
FIG. 26b is an isometric sectional view similar to FIG. 26a, illustrating the vacuum lumen being peeled away from the tissue lumen.
Figure 26C:
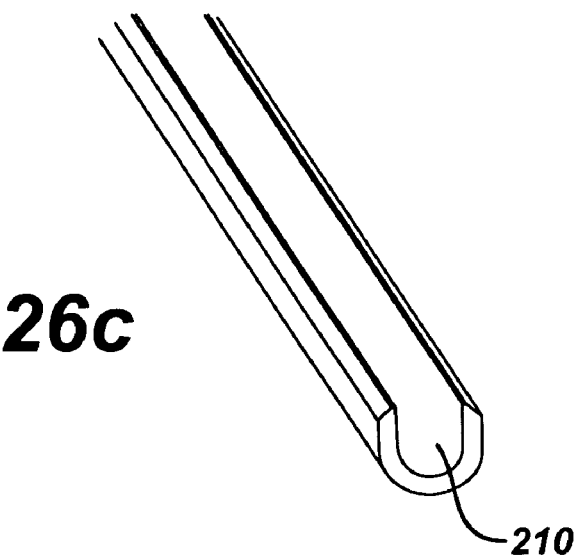
FIG. 26c is an isometric view similar to FIG. 26a, illustrating the tissue lumen removed from the vacuum lumen.

FIGS. 26a–26c illustrate one embodiment for a separable sample storage tube in which a dual lumen tube 280 is extruded with weakened sides along the exterior of tissue lumen 210, as indicated by reference numeral 282, so that a portion of the lumen 210 is separable, such as by peeling, to expose tissue samples. When opposite forces are applied to lumens 210, 214, the two lumens can be peeled apart at the weak points 282, with the upper portion of tissue lumen 210 separating with vacuum lumen 214 as shown in FIG. 26b. The remaining, lower portion of tissue lumen 210 will form an open U-channel containing the stacked tissue samples (U-channel shown in FIG. 26c). The samples may be removed from the opened tissue lumen 210 using a forceps or other instrument.

Figure 27A:
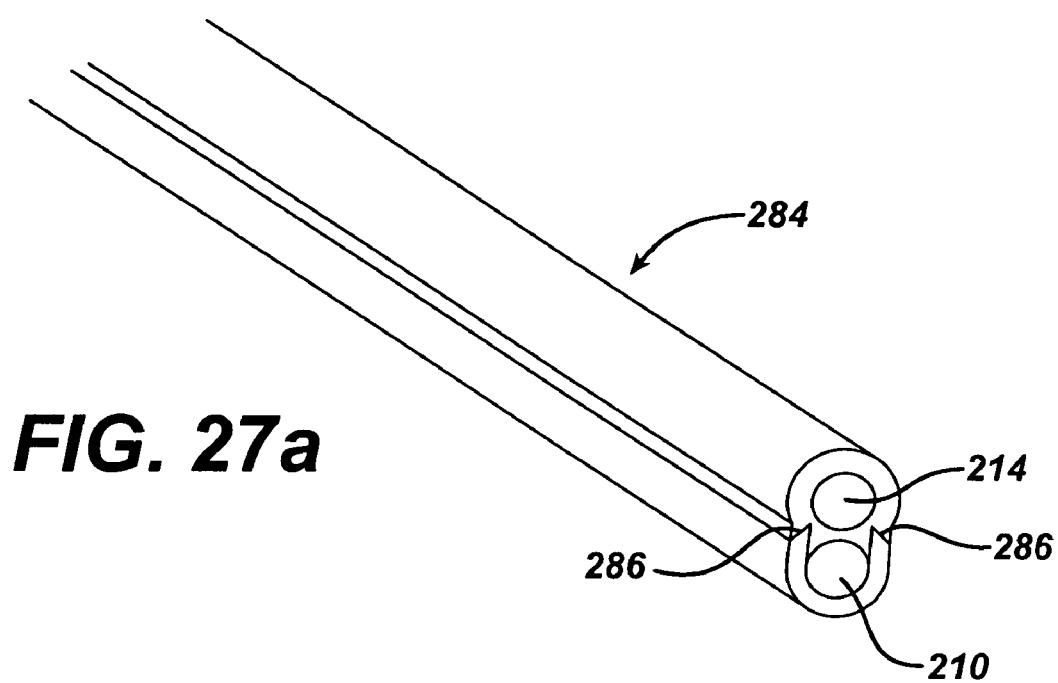
FIG. 27a is an isometric sectional view of an alternative embodiment for a separable tissue sample storage tube.
Figure 27B:
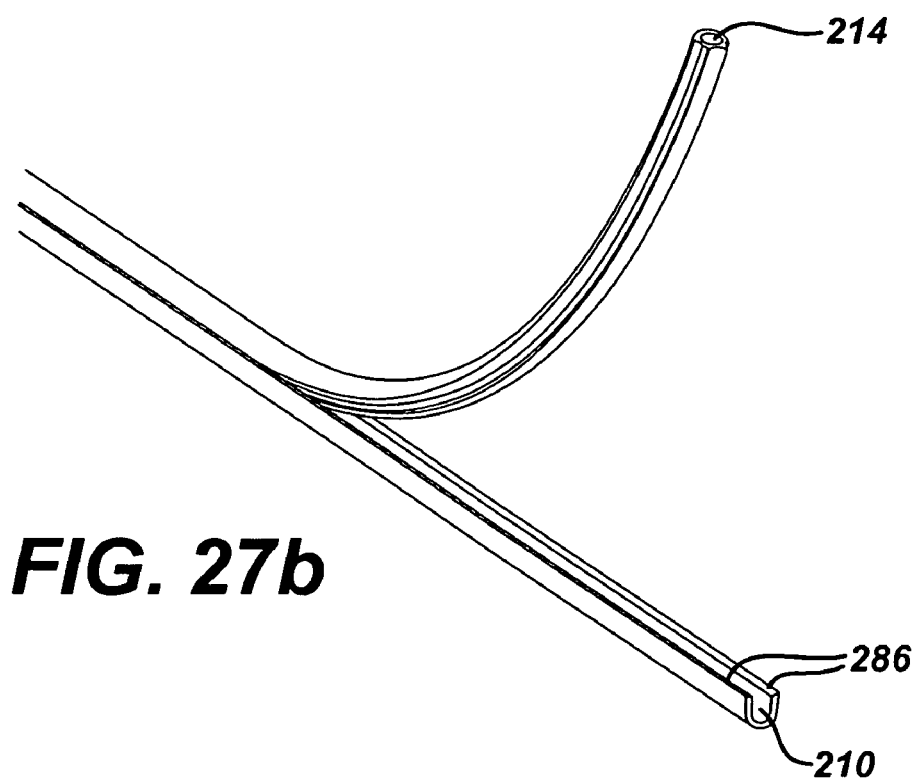
FIG. 27b is an isometric sectional view similar to FIG. 27a, illustrating the vacuum lumen being peeled away from the tissue lumen.

As an alternative to extruding the sample tube with weakened side points 282, tissue and vacuum lumens 210, 214 could be extruded separately and assembled together to form a dual lumen tube 284, an example of which is shown in FIG. 27a. In this embodiment, vacuum lumen 214 is extruded to include the upper portion of tissue lumen 210 so that tissue lumen 210 forms an open U-channel. The tissue and vacuum lumens 210, 214 are joined along the upper edges 286 of the U-channel by an adhesive or other type of fastening mechanism. To access the tissue samples, opposite forces are applied to tube 284 to break the adhesive bond or other fastening means and peel vacuum lumen 214 away from tissue lumen 210, as shown in FIG. 27b. The samples may then be removed from the open tissue lumen.

Figure 28:
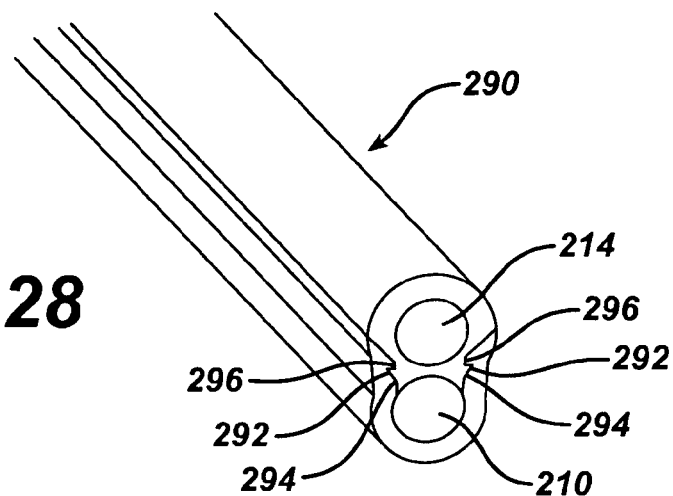
FIG. 28 is an isometric sectional view of a third embodiment for a separable tissue storage tube in which the tissue and vacuum lumens are separately extruded and attached together by a mechanical latch.

In yet another embodiment for a separable sample storage tube, shown in FIG. 28, a dual lumen tube 290 is formed by joining separately extruded vacuum and tissue lumens 210, 214. In this embodiment, vacuum lumen 214 is formed as a closed piece having at least one pair of laterally extending teeth 292. Tissue lumen 210 is formed as an open U-shaped channel having a corresponding number of pairs of laterally extending notches 294 along the inner surfaces of the channel. Teeth 292 are shaped to engage notches 294 to form a mechanical latch 296 that locks vacuum lumen 214 and tissue lumen 210 together to form the sample tube. Pulling vacuum lumen 214 in an opposite direction away from tissue lumen 210 will disengage teeth 292 from notches 294, thereby opening the top of the tissue lumen to remove tissue samples. Mechanical latch 296 may be used in combination with an adhesive or other attachment mechanism to lock the vacuum and tissue lumens together.

Figure 29:
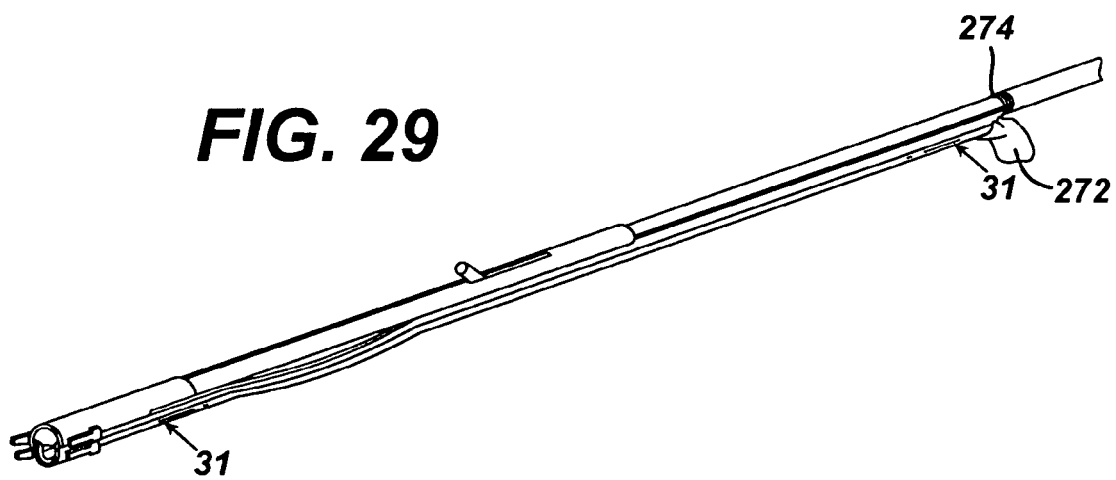
FIG. 29 is an isometric view of an alternative embodiment for the serial tissue stacking assembly of FIG. 14, in which the proximal end of the tissue lumen is attached to a tissue stop rather than the tissue retrieval mechanism.
Figure 30:
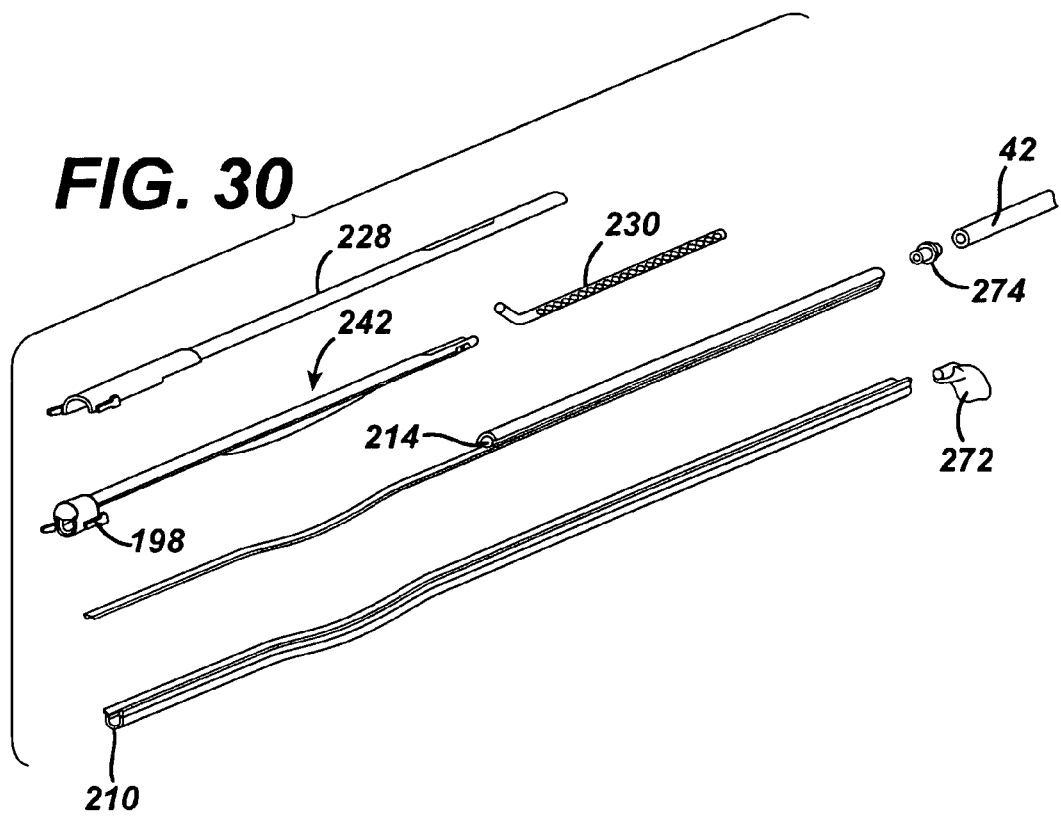
FIG. 30 is an exploded isometric view of the alternative serial tissue stacking assembly embodiment shown in FIG. 29.

FIGS. 29 and 30 illustrate an alternative embodiment for serial tissue stacking assembly 190 where sample storage tube 206 is replaced with a separable sample storage tube shown in FIGS. 26–28. In addition, the tissue retrieval mechanism 260 is replaced with a tissue lumen peel tab 272. A tissue stop feature is located in lumen peel tab 272 at the proximal end of tissue lumen 210. A tubing connector 274 connects the proximal end of vacuum lumen 214 to an axial vacuum line, such as a vacuum line 42 communicating with vacuum source 36. In this embodiment, tissue samples are stacked distally from the tissue stop. The tissue samples 204 can be removed real time by peeling the tissue lumen from the vacuum lumen 214. Alternately, the tissue samples can be removed at the conclusion of the procedure.

Figure 31A:
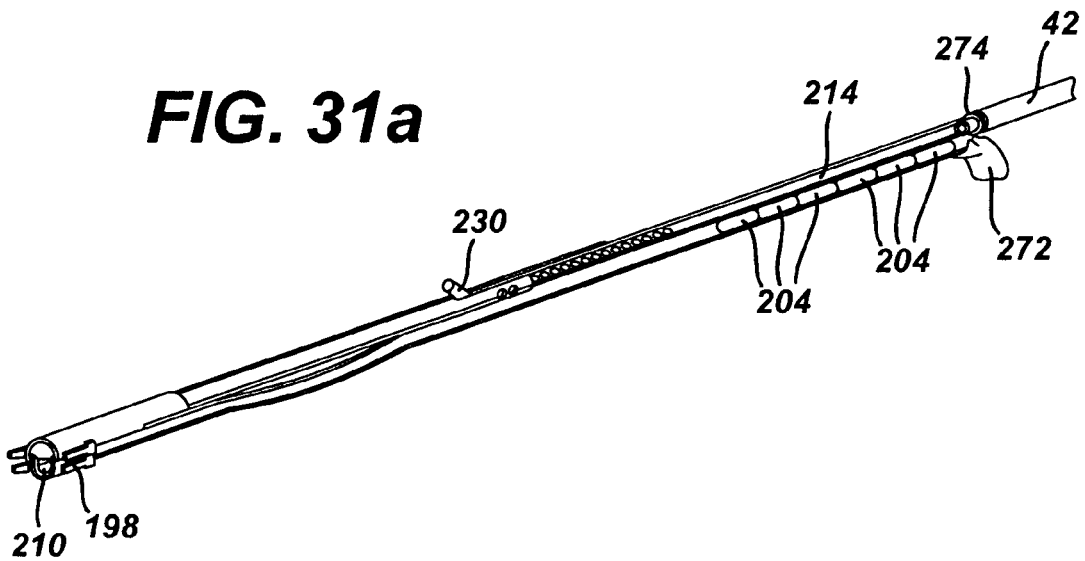
FIG. 31a is an isometric sectional view of the alternative serial tissue stacking assembly embodiment shown in FIG. 29 showing the positions of the connectors, sample tube and translating rod of the serial tissue storing assembly when the cutter and drive carriage are advanced distally in an initial cutting cycle.
Figure 31B:
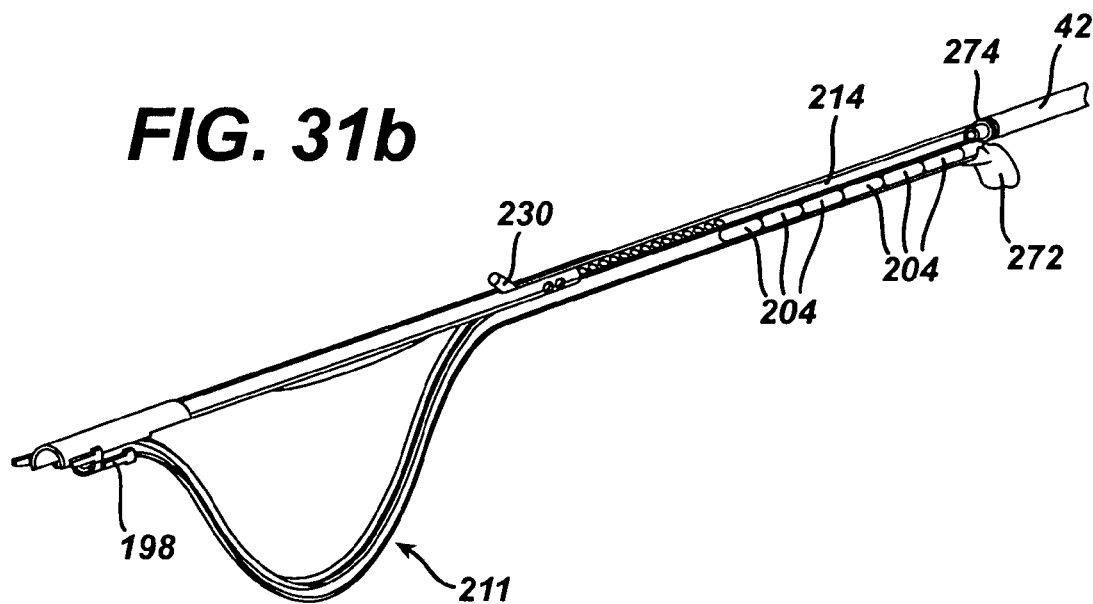
FIG. 31b is an isometric sectional view similar to FIG. 31a, showing the positions of the connectors, sample tube and translating rod when the cutter and drive carriage are retracted following the initial cutting cycle.
Figure 31C:
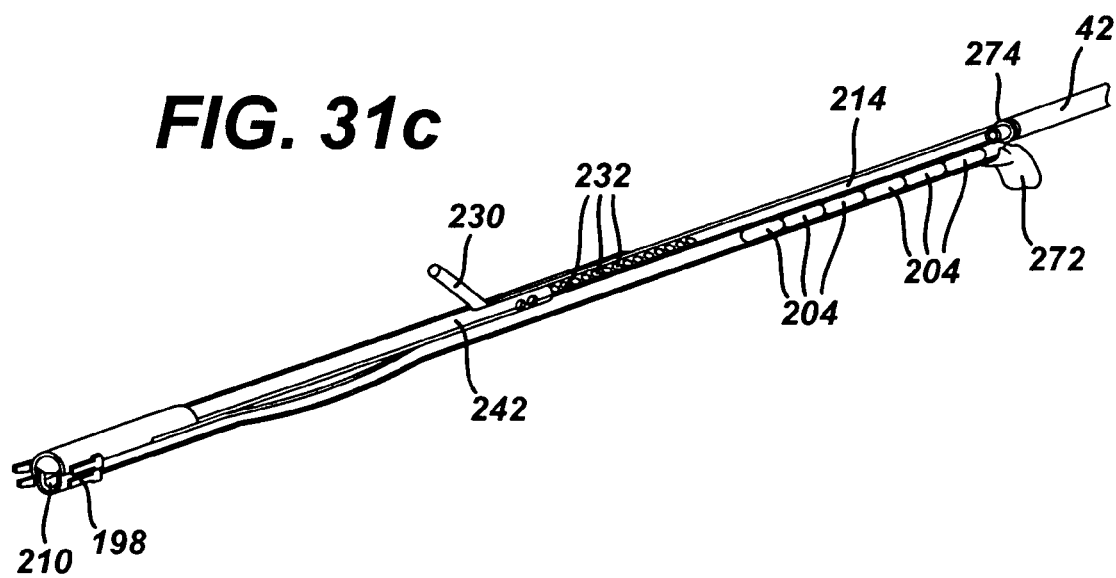
FIG. 31c is an isometric sectional view similar to FIG. 31a, showing the positions of the connectors, sample tube and translating rod of the serial tissue storing assembly when the cutter and drive carriage are advanced distally during a second cutting cycle.
Figure 31D:
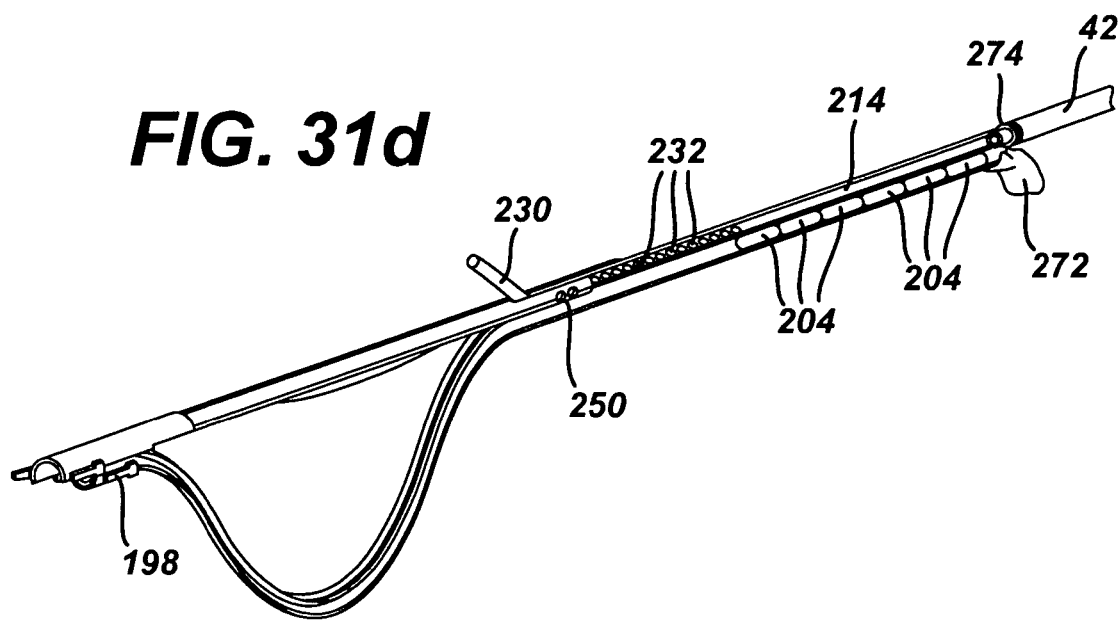
FIG. 31d is an isometric sectional view similar to FIG. 31a, showing the positions of the connectors, sample tube and translating rod of the serial tissue storing assembly when the cutter and drive carriage are retracted following the second cutting cycle.

FIGS. 31a–31d illustrate the advanced and retracted positions of lower connector 198, tissue lumen 210 and rod 230 for the initial two cutting cycles of a biopsy procedure. As shown in FIG. 31a, when cutter 100 is advanced to a fully distal position, i.e. completely through tissue receiving port 86, tissue lumen 210 is advanced fully distal as well, with the tissue lumen substantially parallel to outer sleeve 228. As cutter 100 retracts from tissue receiving port 86 following tissue cutting, tissue lumen 210 retracts with drive carriage 134 to a proximal position, as shown in FIG. 31b. In this position, the a distal length tissue lumen 210 extends downward, such as by flexing, away from outer sleeve 228. Reciprocating member 242 also retracts and grips the next set of ratchet teeth 232 on rod 230. During the next cutting cycle, shown in FIG. 31c, cutter 100 is again fully advanced by drive carriage 134 and lower connector 198 again pulls tissue lumen 210 distally. As lower connector 198 is pulled distally, engagement pawls 250 pull on ratchet teeth 232 of rod 230 to advance the rod through vacuum lumen 214 and out opening 234. At the conclusion of the second cutting cycle, tissue lumen 210 is again retracted proximally as shown in FIG. 31d.

Figure 32:
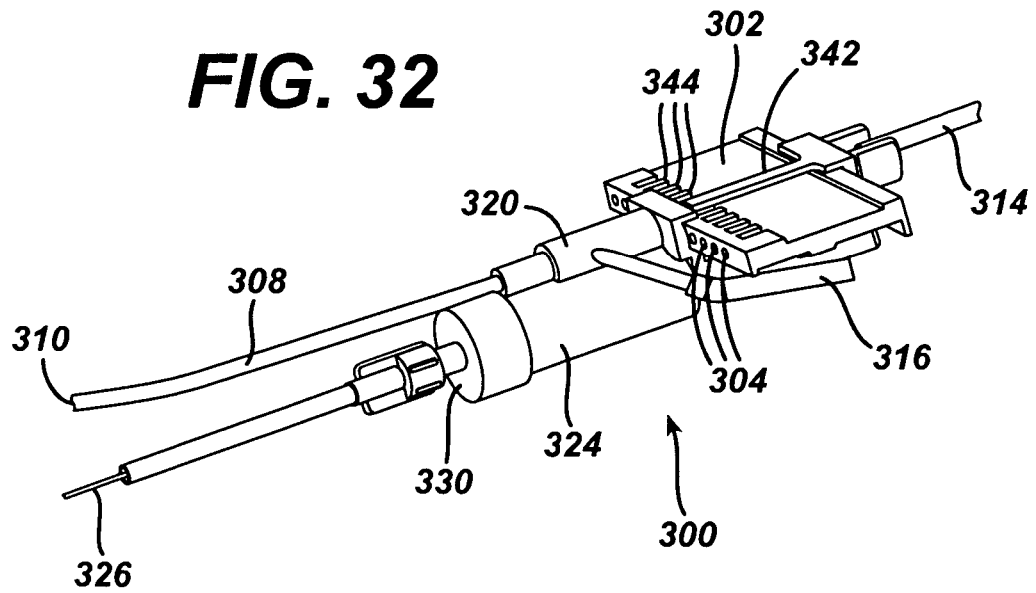
FIG. 32 is an isometric view of a parallel tissue stacking assembly for the present invention.
Figure 33:
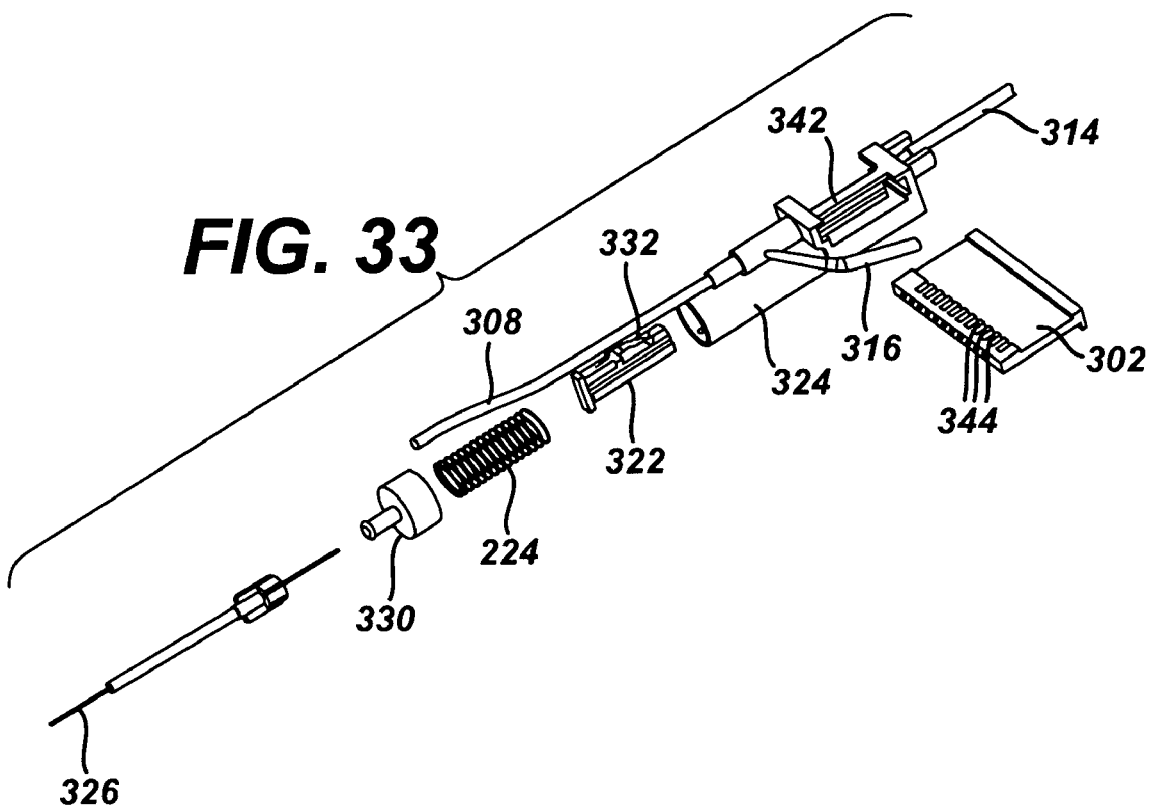
FIG. 33 is an exploded isometric view of the parallel tissue stacking assembly of FIG. 32.
Figure 34:
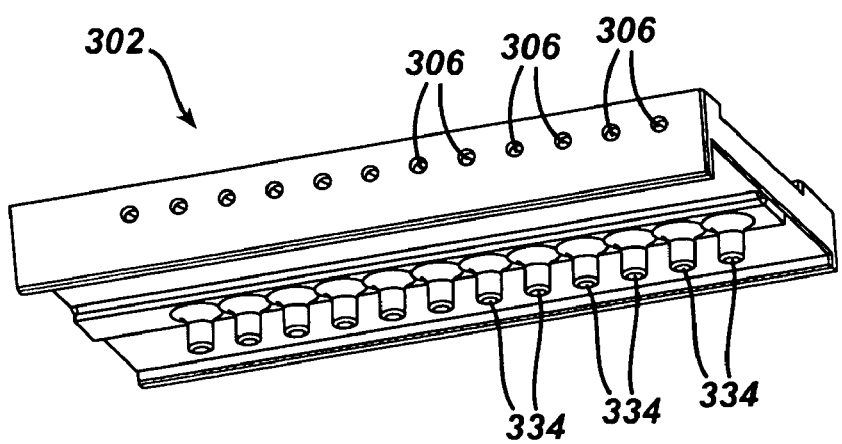
FIG. 34 is a bottom isometric view of the tissue storage component shown in FIGS. 32 and 33.

FIG. 32 illustrates an alternative embodiment for tissue storage assembly 52, in which the storage assembly comprises a parallel tissue stacking assembly 300. In parallel tissue stacking assembly 300, tissue samples are stored one beside the next in a tissue storage component and removed at the end of the procedure. As shown in FIGS. 32 and 33, parallel stacking assembly 300 comprises a tissue storage component 302 containing a series of side-by-side lumens 304. Each of the lumens 304 is slightly longer than the length of tissue receiving port 86 for storing tissue samples aspirated from the receiving port. Component 302 may be comprised of a clear plastic material to allow visual inspection of the tissues samples stored therein. An integrated knock-out pin 306, (FIG. 34), can be provided at the proximal end of each tissue lumen 304 to prevent tissue samples from translating completely through the lumen and into vacuum system 36, while providing vacuum to be communicated to a lumen (eg. each knockout pin 306 can include a small central opening large enough to provide flow communication for providing vacuum to lumen 304, but small enough to not allow a tissue sample to pass out the distal end of lumen 304.)

Figure 35:
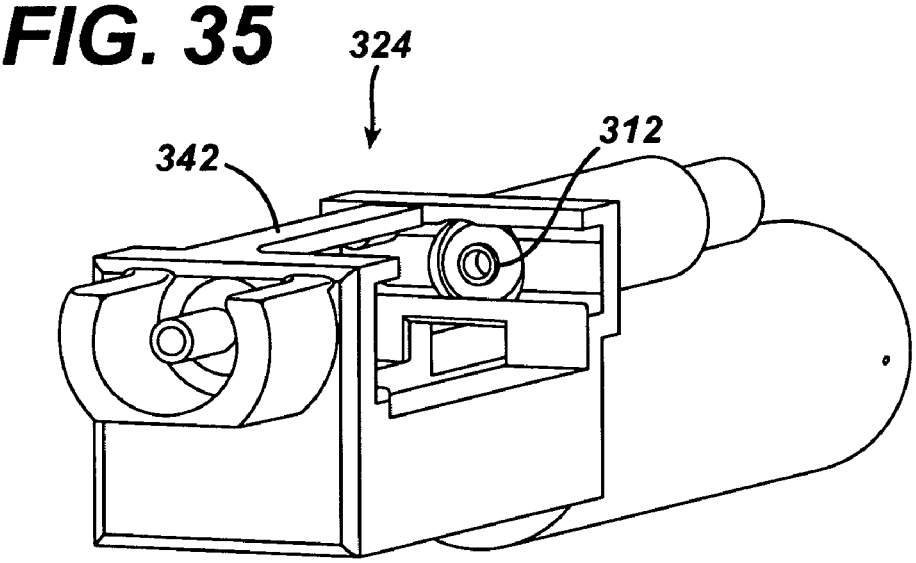
FIG. 35 is an isometric view of the distal end of the parallel tissue stacking assembly of FIG. 32, with the tissue storage component removed.

Returning to FIGS. 32 and 33, a tissue tube 308 having a tissue lumen 310 therein, extends distal of component 302 to connect with tube 152 in probe 32. Tubes 152 and 308 can be aligned to provide a continuous, generally straight line passageway from lumen 104 of cutter 100 to a lumen 304 in component 302. An O-ring seal 312, shown in FIG. 35, can be provided at the proximal end of tissue tube 308 to seal the passageway between tissue lumen 310 and the lumen 304 aligned with tube 308. Sample and tissue tubes 152, 308 may be detachably connected by any suitable type of fastening mechanism such as, for example, snap fasteners similar to those shown in FIGS. 15a and 15b. A first vacuum port 314 can be located on the proximal side of component 302 to provide vacuum to tissue lumen 310 through the lumen 304 aligned with tube 308. A second lateral vacuum port 316 can be employed to provide vacuum to tissue lumen 310 at a position distal of component 302. Each of vacuum ports 314, 316 can be attached to vacuum source 36 through an axial vacuum line 42 to provide vacuum for drawing tissue proximally in lumen 104 of cutter 100. Lateral vacuum port 316 can be attached to a vacuum chamber 320 that surrounds tissue tube 308. Tissue tube 308 can include a plurality of spaced holes within vacuum chamber 320 for communicating vacuum between the chamber and tube lumen 310. Lateral vacuum port 316 and chamber 320 provide additional vacuum for aiding in the proximal movement of a tissue sample (such as in the case where a tissue sample fragments into multiple pieces during sampling).

Figure 36A:
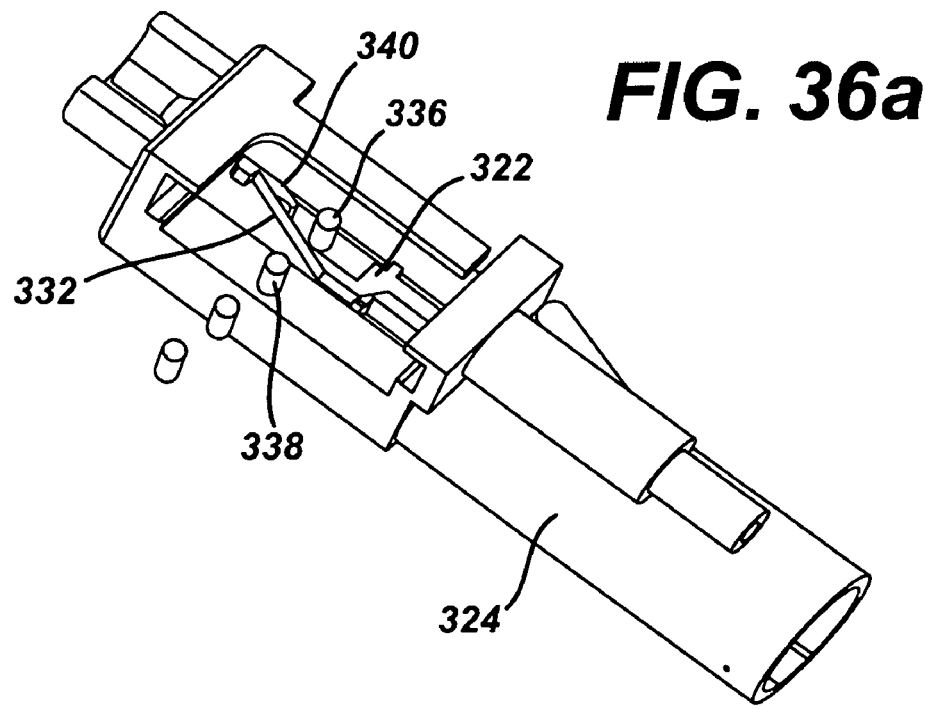
FIG. 36a is a more detailed isometric view of the cam member of FIG. 33, showing the cam member in a retracted position at the beginning of a cutting cycle, with the position of a pair of bosses shown in phantom.
Figure 36B:
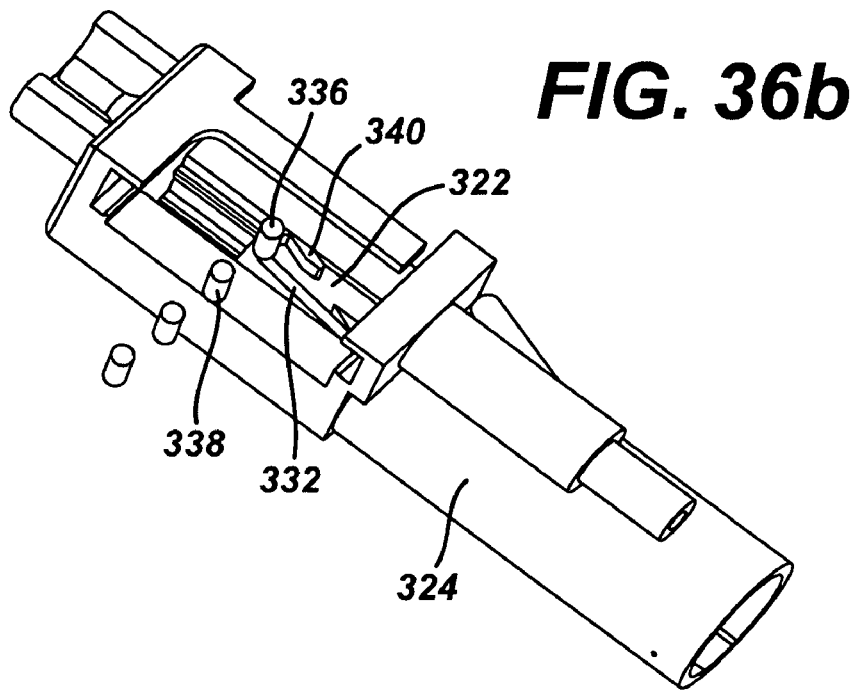
FIG. 36b is a more detailed isometric view similar to FIG. 36a, showing the cam member in an advanced position during the cutting cycle, and a pair of bosses in phantom, with one of the bosses deflecting the camming surface.

After a tissue sample is stored in a lumen 304, component 302 can be indexed laterally to axially align the next adjacent lumen with tissue lumen 310. As shown in FIG. 33, a cam member 322 is provided for indexing component 302. Cam member 322 is located in a housing 324 that extends beneath component 302. Cam member 322 is operatively connected to drive carriage 134 in probe assembly 32 to translate distally and proximally with the drive carriage during each cutting cycle. Cam member 322 is attached to drive carriage 134 by a mechanical cable 326 that extends distally through an end cap 330. Cable 326 is attached to drive carriage 134 and pulls cam member 322 distally as the drive carriage 134 moves distally. As cam member 322 moves, a camming surface 332 on the cam member interacts with bosses 334 (shown in FIG. 34) on the under surface of component 302 to index component 302. Camming surface 332 can comprise an angled, flexible strip of material that is deflected by bosses 334. As shown in FIG. 36a, camming surface 332 is in a non-deflected position between two bosses, identified by phantom bosses 336, 338, when cam member 322 is in a proximal-most position prior to a cutting cycle. As cam member 322 advances distally at the beginning of a cutting cycle, camming surface 332 is deflected out of position by the contact between boss 336 and a first side of the camming surface. As cam member 322 continues to advance distally, boss 336 deflects camming surface 332 to a point at which the boss passes through an opening created between the cam surface and a stop block 340, as shown in FIG. 36b. After boss 336 passes through the opening created by the deflecting camming surface, the camming surface springs back into a non-deflected position in contact with stop block 340.

Figure 36C:
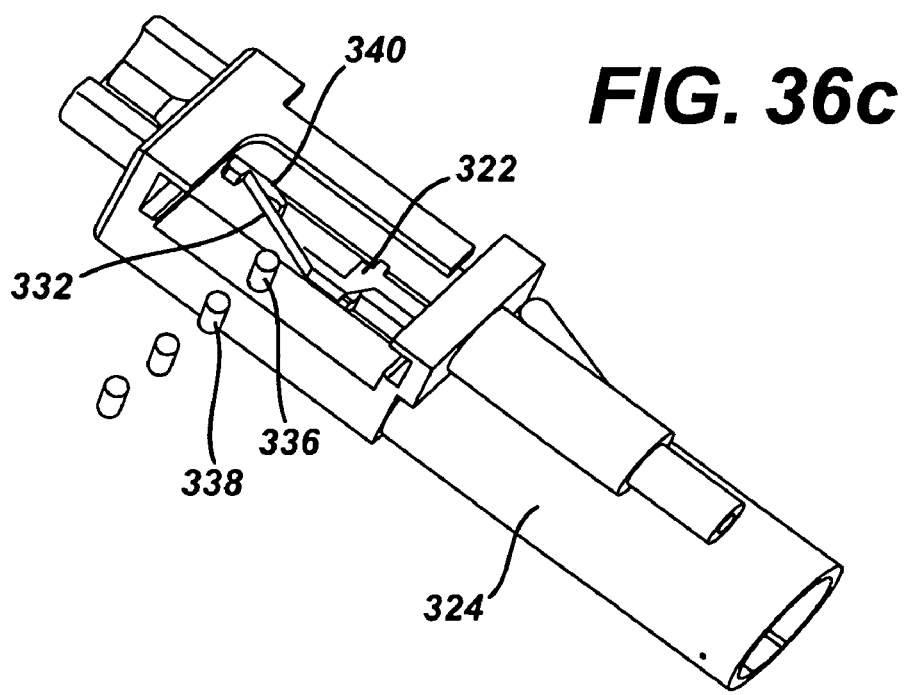
FIG. 36c is a more detailed isometric view similar to FIG. 36a, showing the cam member in a retracted position at the conclusion of a cutting cycle, with the position of a boss at the conclusion of the cutting cycle shown in phantom.

When drive carriage 134 begins to retract following the cutting of tissue, a return spring 224 within the distal end of housing 324 pushes cam member 322 proximally within the housing. As cam member 322 retracts proximally, the opposite side of camming surface 332 contacts boss 336. As cam member 322 continues to retract, the angle in camming surface 332 causes boss 336 to be pushed laterally, as shown in FIG. 36c. As boss 336 is pushed laterally, component 302 is indexed laterally relative to tissue tube 308, thereby positioning the next adjacent lumen 304 to receive the next tissue sample through tube 308. As shown in FIGS. 32 and 33, component 302 is positioned between cam member housing 324 and a detent arm 342. Detent arm 342 extends distally across the upper surface of component 302. As component 302 is indexed laterally by the interaction of camming surface 332 and boss 336, detent arm 342 engages one of a series of indexing detents 344. Indexing detents 344 lock the next active lumen 304 into alignment with lumen 310 following each indexing action. The plurality of bosses 334 and indexing detents 344 enable component 302 to be repetitively indexed to store a plurality of tissue samples during a biopsy procedure. At the conclusion of a biopsy procedure, component 302 may be removed from between housing 324 and detent arm 342, and the tissue samples removed from the individual tissue lumens 304. The top surface of component 302 can include a cover or other removable portion to allow each sample to be easily removed from the lumens 304.

Figure 37:
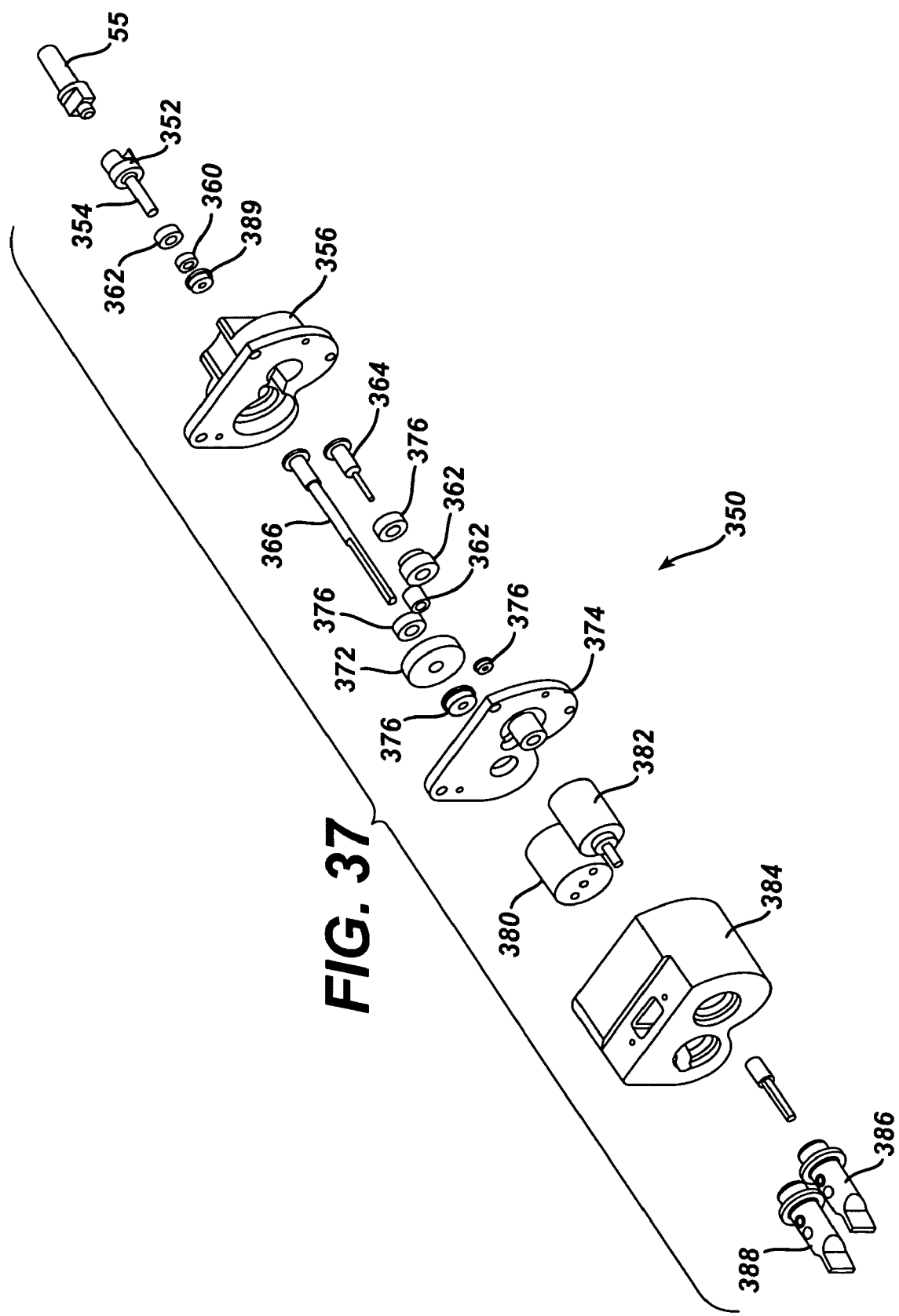
FIG. 37 is an exploded isometric view of a cable driven drive assembly for the holster viewed in the proximal direction.

FIG. 37 is an exploded isometric view of an exemplary drive assembly 350 for holster 34. In the assembly shown in FIG. 37, the translation and rotation drive trains (for providing rotation and translation of cutter 100) are driven by a single rotatable cable 55 (also shown in FIG. 1) that extends between holster 34 and a remotely located motor, such as a motor in control module 46. A single drive cable is capable of rotating both drive trains due to the reduced cutter stroke of the present invention. The reduced cutter stroke enables the size of handpiece 30, as well as the load on the drive motor, to be reduced relative to previous biopsy devices. Powering handpiece 30 through a single rotatable cable enables the handpiece to be utilized in MRI guided procedures since ferromagnetic motor components are separated from the handpiece. The handpiece can also be used in mammography and ultrasound guided procedures. Accordingly, a common probe assembly and handpiece can be utilized for multiple imaging environments. For an MRI guided procedure, the length of the rotatable cable may be increased to accommodate use near or within an MRI bore.

In the embodiment shown in FIG. 37, rotatable cable 55 attaches to a drive cable input coupling 352 for providing rotational drive to holster 34. A drive shaft 354 from input coupling 352 extends to a proximal housing 356. Within proximal housing 356, an input gear 360 is mounted on input drive shaft 354 between spacer 362 and bearing 389 so as to engage corresponding gears on a translation drive shaft 364 and a rotation drive shaft 366. The interaction of the input gear 360 with translation shaft gear 370 and rotation shaft gear 372 transmits the rotational drive to translation and rotation drive shafts 364, 366. Translation and rotation drive shafts 364, 366 extend from proximal housing 356 through a pair of bores in a center housing 374. Translation and rotation gears 370, 372 are spaced between the proximal and center housings by bearings 376.

Distal of center housing 374, holster 34 includes a rotary encoder 380 for providing a feedback signal to control module 46 regarding rotation of the drive shafts. Encoder 380 may be mounted on either the translation or the rotation drive shafts. Holster 34 also includes an optional planetary gearbox 382 on translation drive shaft 364. Gearbox 382 provides a gear reduction between the translation and rotation drive trains to produce differing speeds for the translation of drive carriage 134 and the rotation of cutter 104. Distal of gearbox 382 and encoder 380, drive assembly 350 includes a housing 384. Housing 384 includes connections for coupling the translation drive train with translation drive input shaft 386, and the rotational drive train with rotary drive input shaft 388. Each of the drive input shafts 386, 388 has a distal end shaped to operatively engage slots on corresponding drive shafts in probe assembly 32. In particular, translation drive input shaft 386 is shaped to engage slot 128 of translation shaft 142 (shown in FIG. 4), and rotary drive input shaft 388 is shaped to engage slot 132 of rotary drive shaft 114. As mentioned above with respect to FIG. 6, the drive input shafts may have molded interfaces, rather than the mating slots and tips shown in FIGS. 4 and 37, to reduce the coupling length between the shafts. Translation and rotary drive shafts 386, 388 extend distally from housing 384 for engagement with drive and translation shafts 114, 142 when probe assembly 32 and holster 34 are connected.

The embodiment shown in FIG. 37 comprises a single drive cable input for operatively driving the translation and rotation shafts. In an alternative embodiment, a single motor mounted in the holster 34 can replace rotatable cable 55. The single motor drives both the translation and rotation shafts through a suitable gearing assembly. The motor may be mounted above or proximal to the drive assembly. Another embodiment replaces the single motor with two motors. One motor would drive the translation drive input shaft and the other would drive the rotary drive input shaft.

In the embodiments described, the cutting stroke length for the cutter 100 is reduced to slightly longer than the length of tissue receiving port 86. This stroke reduction is possible in part because tissue samples are aspirated through the cutter lumen, rather than being pulled proximally through the needle by a retracting cutter. Reducing the cutting stroke length has a number of benefits. One of the benefits of a reduced cutting stroke length is that the overall size and weight of the probe assembly may be reduced, thereby enabling the biopsy device to be used in imaging environments where size has traditionally been a limitation. In particular, the reduced size of the probe assembly enables an essentially common probe assembly to be used in both open and closed bore MRI guided procedures, as well as in mammography and ultrasound procedures, with minor adjustments. A common cable driven holster may also be used in each of the imaging modalities, with the alternative, single or double motor embodiments useable in both the mammography and ultrasound guided procedures. In addition, a common control module can be used to control the handpiece in any of the three imaging environments. The probe assembly may be adapted for use in an MRI guided procedure by utilizing a needle and cutter subassembly that is comprised of a non-ferromagnetic material, such as a plastic or ceramic, in order to reduce image artifacts. In addition, the cutter assembly may be removed from the probe, as described above with respect to FIGS. 7 and 8, for MRI imaging prior to initiation of a cutting cycle. Alternately, the distal end of the cutter may be simply retracted proximally from the tissue receiving port area during imaging.

To accommodate each of the different imaging modalities, reusable handpiece base units specific to each of the imaging environments may be utilized. Each of the handpiece base units may be used for firing and/or rotating the needle aperture, depending upon the operator's needs and the constrictions of the particular imaging environment. Each of the base units is designed to accommodate the probe assembly to enable the same probe to be used across imaging modalities.

Figure 38A:
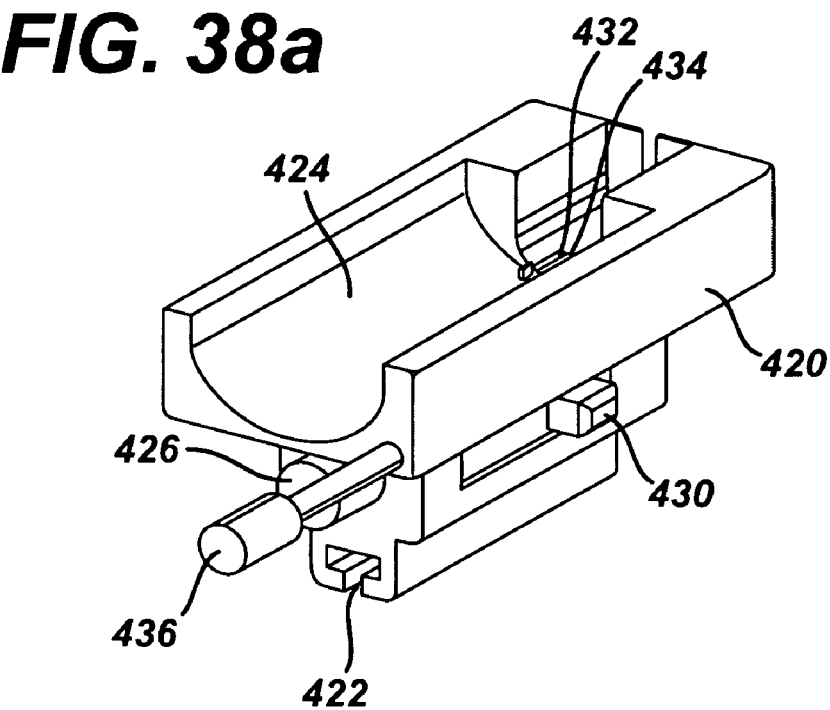
FIG. 38a is an isometric view of a probe assembly base unit for use in a mammography guided biopsy procedure.

FIG. 38a illustrates a base 420 for use with probe assembly 32 in a mammography guided procedure. Base 420 may be attached to the stereotactic arm of a mammography machine by a mounting feature 422. A recessed nest area 424 is provided in base 420 for accommodating the probe lower shell. Probe assembly 32 may be lodged in nest 424 prior to the initiation of a procedure. A firing button 426 is included in base 420 for firing the needle of the probe assembly into the tissue mass of interest. A knob 430 on the side of base unit 420 compresses a firing spring within the unit. When button 426 is compressed, the spring pushes against probe assembly 32 to forcibly drive the entire probe assembly and nest 424 forward relative to the mounting feature 422.

Figure 38B:
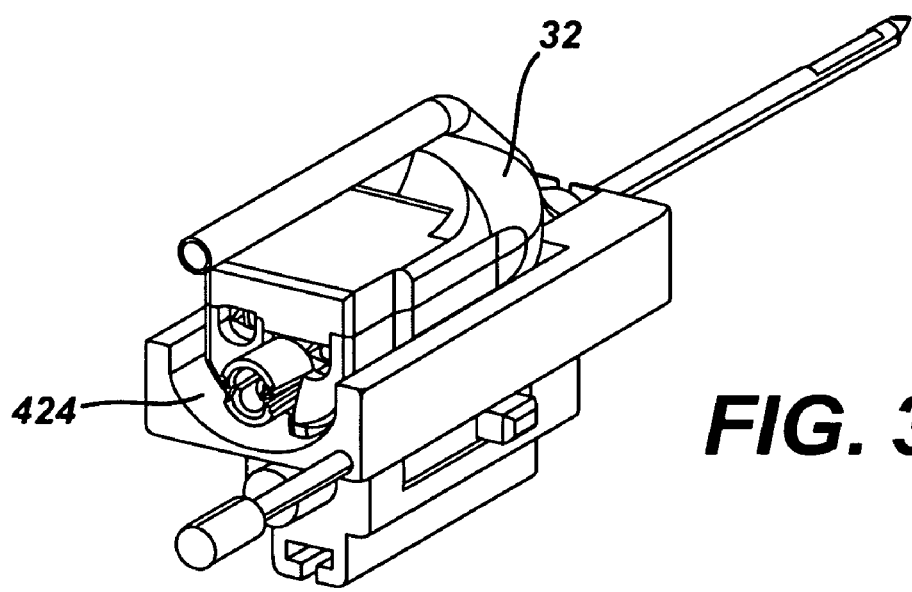
FIG. 38b is an isometric view of a probe and probe assembly base unit for use in a mammography guided biopsy procedure.

An aperture rotation gear 432 is also provided in the recessed area of base 420 for rotating the tissue receiving port of the probe assembly after the needle is positioned within the tissue mass. Aperture rotation gear 432 includes a plurality of gear teeth 434. Gear teeth 434 project partially above the recessed surface area to engage similar shaped teeth on a second gear integral to the needle support component within probe assembly 32. Teeth on the second, needle gear are recessed within the probe shell, but accessible by aperture rotation gear 432 when the probe is lodged in nest 424. A knob 436 is provided on the proximal end of base 420 for manually rotating gear 432. When gear 432 rotates, the engagement between the gears causes the needle to rotate, thereby repositioning the tissue receiving port within the tissue mass. Probe assembly 32 can include flexible engagement fingers that lock the needle gear and prevent the gear from rotating outside of nest 424. When probe assembly 32 is inserted into nest 424, the flexible fingers are deflected so as to disengage from the needle gear, and allow the gear to rotate in response to the rotation of base gear 432. FIG. 38b illustrates the probe assembly 32 lodged in nest 424.

Figure 39:
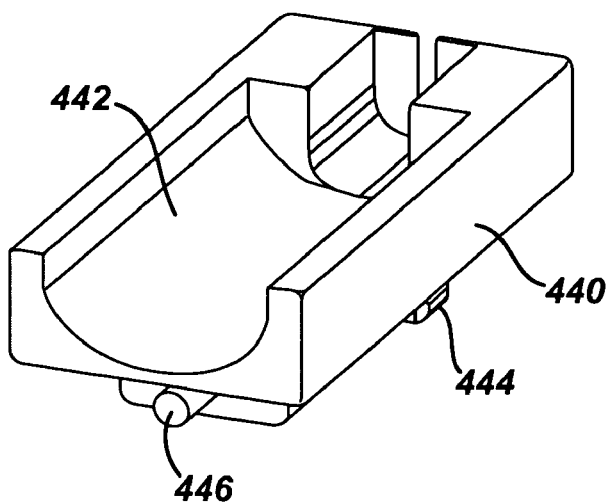
FIG. 39 is an isometric view of a second embodiment of a probe assembly base unit for use in an ultrasound guided biopsy procedure.

FIG. 39 illustrates a similar type of probe base unit for use in an ultrasound imaging environment. As shown in FIG. 39, the base unit 440 includes a nest 442 for accommodating the lower shell of probe assembly 32. A knob 444 is provided for compressing a firing spring within base 440, as well as a button 446 for releasing the spring to "fire" the probe assembly and nest 424 into a tissue mass. In the ultrasound environment, base 440 may be hand-held and manipulated as required by the operator. Accordingly, a needle rotation mechanism is not necessary for base 440, since the operator may rotate the needle by manually rotating the base and/or probe assembly.

Figure 40:
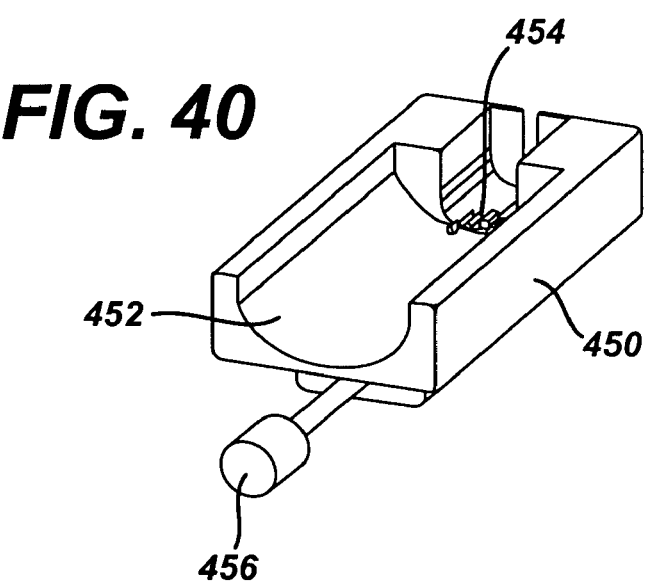
FIG. 40 is an isometric view of a third embodiment of a probe assembly base unit for use in an MRI guided biopsy procedure.

As shown in FIG. 40, a third type of probe base 450 is provided for use in MRI guided procedures. Base 450 may be mounted to a localization unit within the MRI unit. The reduced size of the probe assembly in the present invention reduces the structural requirements for the localization unit due to the reduced cantilever loading generated by the probe. MRI base 450 includes a recessed nest 452 for accommodating the lower probe shell. In addition, the base includes an aperture rotation gear 454 having a plurality of gear teeth that engage similar shaped teeth that extend from the probe lower shell. The gear in the lower probe shell is attached to the needle to rotate the needle whenever gear 454 is rotated, in a manner similar to the mammography nest embodiment shown in FIG. 38. An aperture rotation knob 456 is located on the proximal end of base 450 to manually rotate gear 454 and, correspondingly, the tissue receiving aperture in the needle. Base 450 does not require a firing mechanism for positioning the needle within the tissue. However, multiple needle lengths may be used with the probe assembly to enable the probe assembly to more easily fit within the MRI unit. The particular needle length selected will depend upon the depth of the tissue mass of interest within the patient's body.

Figure 41:
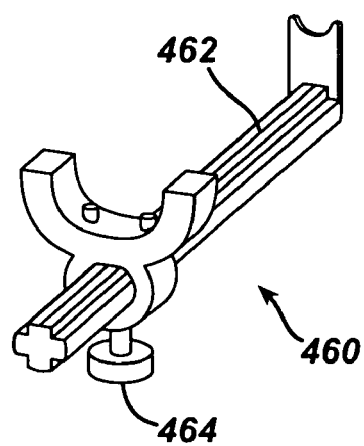
FIG. 41 is an isometric view of an MRI localization depth gage for interfacing the probe assembly with an MRI unit.

As an alternative to the use of MRI base 450, an MRI localization depth gage 460, such as shown in FIG. 41, may be used for positioning the probe assembly. In this embodiment, a depth stop 462 is attached to the probe assembly and/or the needle 80. The depth stop includes an adjustment knob 464 for adjusting the desired depth of the probe needle. After the needle is properly positioned, the probe is inserted into the patient's tissue until the stop is reached. The patient may then be placed in the MRI device and imaged without additional support for the probe assembly. After the needle position within the tissue is confirmed, the holster is attached to the probe assembly to begin tissue sampling.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention can be alternatively described as a means for performing that element's function.

What is claimed:

1. A method of providing a biopsy sample comprising:
   providing an outer cannula having a cutter lumen, a side tissue port communicating with the cutter lumen, and a fluid passageway distal of the side tissue port and spaced circumferentially from the side tissue port;
   providing a hollow cutter disposed for translation within the cutter lumen;
   providing a second lumen, wherein the second lumen is parallel to the cutter lumen, wherein the second lumen is in fluid communication with the cutter lumen via the fluid passageway;
   drawing tissue into the side tissue port, wherein the act of drawing tissue comprises:
   (i) inducing a vacuum in the cutter lumen, and
   (ii) inducing a vacuum in the second lumen;
   translating a distal end of the cutter past the side tissue port to sever a tissue sample;
   directing a fluid through the fluid passageway to push the severed tissue sample through the cutter.

2. The method of claim 1 wherein the step of directing a fluid through the fluid passageway is performed while the distal end of the cutter is disposed distal of the side tissue port.

3. The method of claim 1 wherein the fluid passageway is spaced at least 90 degrees circumferentially from the side tissue port.

4. The method of claim 1 wherein the fluid passageway is disposed circumferentially opposite the side tissue port.

5. The method of claim 1 wherein the step of directing a fluid through the fluid passageway is performed with the inner cutter disposed concentrically within the cutter lumen.

6. The method of claim 1 wherein the step of directing a fluid is performed without directing fluid past the side tissue port.

7. The method of claim 1 wherein the step of directing a fluid comprises directing a liquid.

8. The method of claim 1 wherein the act of pushing the severed tissue sample and the act of inducing a vacuum within the hollow cutter are performed substantially simultaneously.

* * * * *